United States Patent [19]

Chucholowski et al.

[11] Patent Number: 5,153,226

[45] Date of Patent: Oct. 6, 1992

[54] ACAT INHIBITORS FOR TREATING HYPOCHOLESTEROLEMIA

[75] Inventors: Alexander W. Chucholowski, Bad Krozingen, Fed. Rep. of Germany; Mark W. Creswell, Chelsea, Mich; William H. Roark; Ila Sircar, both of Ann Arbor, Mich.

[73] Assignee: Warner-Lambert Company, Morris Plains, N.J.

[21] Appl. No.: 557,204

[22] Filed: Jul. 30, 1990

Related U.S. Application Data

[63] Continuation-in-part of Ser. No. 401,367, Aug. 31, 1989, abandoned.

[51] Int. Cl.$^5$ .................. A61K 31/18; A61K 31/165
[52] U.S. Cl. .................................... 514/617; 514/618; 514/619; 514/620; 514/621; 514/622; 514/626; 514/255; 514/238.2; 514/414; 514/419; 514/378; 514/374; 514/399; 514/463; 514/385; 564/164; 564/165; 564/167; 564/166; 564/194; 544/165; 544/400
[58] Field of Search ............... 564/164, 165, 166, 167, 564/168, 194; 514/617, 618, 619, 620, 621, 622, 626, 255, 238.2, 414, 419, 378, 374, 403, 399, 385

[56] References Cited

U.S. PATENT DOCUMENTS

| | | | |
|---|---|---|---|
| 4,218,477 | 8/1980 | Boyes et al. | 424/324 |
| 4,310,429 | 1/1982 | Lai | 252/51.5 A |
| 4,500,662 | 2/1985 | Lai | 524/99 |
| 4,639,468 | 1/1987 | Roncucci et al. | 514/620 |
| 4,891,058 | 1/1990 | Wee | 71/118 |
| 4,944,796 | 7/1990 | Wee | 71/118 |
| 4,987,153 | 1/1991 | Kay et al. | 514/620 |

Primary Examiner—Richard L. Raymond
Assistant Examiner—Mark W. Russell
Attorney, Agent, or Firm—Ruth H. Newtson

[57] ABSTRACT

The present invention are novel amino acid amide compounds of the following general formula which inhibit the enzyme acylcoenzyme A:cholesterol acyltransferase:

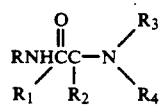

wherein R is phenyl or 1- or 2-naphthyl which are unsubstituted or may be substituted; $R_1$ is hydrogen or a straight or branched alkyl group having from 1 to 6 carbon atoms; $R_2$ is hydrogen, an aliphatic group, an aromatic group, an aralkyl or diarylalkyl group or $R_1$ and $R_2$ form a carbocyclic group; $R_3$ is hydrogen, an aliphatic group, an aralkyl group wherein the alkyl moiety may contain a carbocyclic entity; $R_4$ is hydrogen, an aliphatic group, $SO_2R_{14}$, $-C(=S)NHR_{15}$, $-CO_2R_{15}$, $-COR_{18}$, or $-C(=O)NHR_{15}$ wherein $R_{14}$ is morpholino, phenyl or substituted phenyl; $R_{15}$ is an alkyl group, phenyl or phenylalkyl wherein the phenyl group may be substituted; and $R_{18}$ is the same is $R_{15}$ or is halo-substituted alkyl, 9-fluoroenylmethylene or pyrrolidino.

1 Claim, No Drawings

ACAT INHIBITORS FOR TREATING HYPOCHOLESTEROLEMIA

CROSS REFERENCE TO RELATED APPLICATION

This application is a continuation-in-part of application Ser. No. 401,367 filed Aug. 31, 1989 now abandoned.

BACKGROUND OF THE INVENTION

This invention relates to chemical compounds having pharmacological activity, to pharmaceutical compositions which include these compounds, and to a pharmaceutical method of treatment. More particularly, this invention concerns certain amino acid amide compounds which inhibit the enzyme acylcoenzyme A:-cholesterol acyltransferase (ACAT), pharmaceutical compositions containing these compounds, and a method of treating hypercholesterolemia and atherosclerosis. This invention also describes novel intermediates useful in preparing the pharmaceutically active compounds of this invention.

In recent years the role which elevated blood plasma levels of cholesterol plays in pathological conditions in man has received much attention. Deposits of cholesterol in the vascular system have been indicated as causative of a variety of pathological conditions including coronary heart disease.

Initially, studies of this problem were directed toward finding therapeutic agents which would be effective in lowering total serum cholesterol levels. It is now known that cholesterol is transported in the blood in the form of complex particles consisting of a core of cholesteryl esters plus triglycerides and an exterior consisting primarily of phospholipids and a variety of types of protein which are recognized by specific receptors. For example, cholesterol is carried to the sites of deposit in blood vessels in the form of low density lipoprotein cholesterol (LDL cholesterol) and away from such sites of deposit by high density lipoprotein cholesterol (HDL cholesterol).

Following these discoveries, the search for therapeutic agents which control serum cholesterol turned to finding compounds which are more selective in their action; that is, agents which are effective in elevating the blood serum levels of HDL cholesterol and/or lowering the levels of LDL cholesterol. While such agents are effective in moderating the levels of serum cholesterol, they have little or no effect on controlling the initial absorption of dietary cholesterol in the body through the intestinal wall.

In intestinal mucosal cells, dietary cholesterol is absorbed as free cholesterol which must be esterified by the action of the enzyme acyl-CoA: cholesterol acyltransferase (ACAT) before it can be packaged into the chylomicrons which are then released into the blood stream. Thus, therapeutic agents which effectively inhibit the action of ACAT prevent the intestinal absorption of dietary cholesterol into the blood stream or the reabsorption of cholesterol which has been previously released into the intestine through the body's own regulatory action.

SUMMARY OF THE INVENTION

The present invention provides a class of compounds which have acyl-coenzyme A: cholesterol acyltransferase (ACAT) inhibitory activity and intermediates useful in preparing said compounds having the following general Formula I:

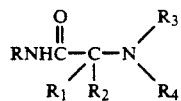

Formula I wherein R is
(a) phenyl$(CH_2)_n$— wherein n is zero to 2 and wherein the phenyl ring is unsubstituted or is substituted with from 1 to 3 substituents selected from
alkyl having from 1 to 6 carbon atoms and which is straight or branched,
alkoxy having from 1 to 6 carbon atoms and which is straight or branched,
phenoxy,
hydroxy,
fluorine,
chlorine,
bromine,
nitro,
trifluoromethyl,
—COOH,
—COOalkyl wherein alkyl has from 1 to 4 carbon atoms
—$NR_5R_6$ wherein $R_5$ and $R_6$ are independently hydrogen or straight or branched alkyl of from 1 to 4 carbon atoms;
(b) 1- or 2-naphthyl which is unsubstituted or substituted with from one to three substituents selected from
alkyl having from 1 to 6 carbon atoms and which is straight or branched;
alkoxy having from 1 to 6 carbon atoms and which is straight or branched,
hydroxy,
fluorine,
chlorine,
bromine,
nitro,
trifluoromethyl,
—COOH,
—COOalkyl wherein alkyl has from 1 to 4 carbon atoms
—$NR_5R_6$ wherein $R_5$ and $R_6$ are as defined above;
wherein $R_1$ is
(a) hydrogen, or
(b) alkyl having from 1 to 6 carbon atoms and is straight or branched;
wherein $R_2$ is
(a) hydrogen;
(b) a straight or branched hydrocarbon chain having 1 to 20 carbon atoms and which is saturated or contains from 1 to 3 double bonds;
(c) p-phenylmethoxybenzyl;
(d)

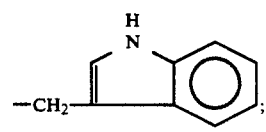

(e) —$CH_2CH_2S(O)_{0-2}$—$CH_3$;
(f) phenyl, 1- or 2-naphthyl which is unsubstituted or is substituted with one or two substituents selected from alkyl having from 1 to 4 carbon atoms and which is straight or branched, alkoxy having from 1 to 4 carbon atoms, hydroxy, chlorine, fluorine, bromine, trifluoromethyl, or amino;

(g) the group

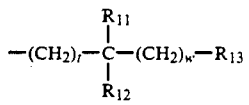

wherein t is zero to 4; w is zero to 4 with the proviso that the sum of t and w is not greater than 5; $R_{11}$ and $R_{12}$ are independently selected from hydrogen or alkyl having from 1 to 6 carbon atoms, or when $R_{11}$ is hydrogen, $R_{12}$ can be selected from the groups defined for $R_{13}$; and $R_{13}$ is an aromatic monocyclic heterocyclic group having from one to three oxygen, sulfur, or nitrogen atoms, phenyl, 1- or 2-naphthyl, or phenyl 1- or 2-naphthyl substituted with from one to three substituents selected from straight or branched alkyl having from 1 to 6 carbon atoms, straight or branched alkoxy having from 1 to 6 carbon atoms, phenoxy, hydroxy, fluorine, chlorine, bromine, nitro, trifluoromethyl, —COOH, COOalkyl wherein alkyl has from 1 to 4 carbon atoms, or —NR$_5$R$_6$ wherein R$_5$ and R$_6$ have the meanings defined above, —CH$_2$NR$_5$R$_6$ wherein R$_5$ and R$_6$ have the meanings defined above; or (h) $R_1$ and $R_2$ taken together with the carbon atom to which they are attached form a saturated carbocyclic ring having from 3 to 7 carbon atoms;

$R_3$ is (a) hydrogen (b) a straight or branched hydrocarbon chain having from 1 to 20 carbon atoms and which is saturated or contains from 1 to 3 double bonds;

(c) the group

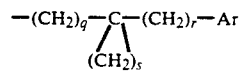

wherein q is zero to 3; r is zero to 2; s is 2 to 6; and Ar is phenyl, 1- or 2-naphthyl, phenyl or 1- or 2- naphthyl substituted with alkyl of from 1 to 6 carbon atoms, and which is straight or branched, alkoxy of from 1 to 6 carbon atoms, and which is straight or branched, hydroxy, benzyloxy, fluorine, chlorine, bromine, nitro, trifluoromethyl,

—NH—COCH$_3$,

—CONH$_2$,

—COOH,

—COOalkyl wherein alkyl has from 1 to 4 carbon atoms, and is straight or branched,

—CH$_2$COOH,

—CH$_2$CONH$_2$,

—NR$_7$R$_8$ wherein R$_7$ and R$_8$ are independently hydrogen, alkyl of from 1 to 6 carbon atoms the terminal carbon of which optionally is substituted with an OR$_9$ group where R$_9$ is hydrogen, alkyl of from 1 to 6 carbon atoms, alkanoyl having from 2 to 5 carbon atoms, benzoyl, or R$_5$ and R$_6$ taken together with the nitrogen atom to which they are attached form a 5- or 6-membered ring optionally interrupted by an oxygen atom or —NR$_9$; wherein R$_9$ is as defined above;

—CH$_2$NR$_7$R$_8$ where R$_7$ and R$_8$ are as defined above;

—CH$_2$OR$_9$ where R$_9$ is as defined above;

—COO—alkyl where alkyl is from 1 to 6 carbons and is straight or branched and the terminal carbon of which optionally is substituted with an OR$_9$ group or NR$_7$R$_8$ where R$_7$, R$_8$, and R$_9$ are as defined above;

—NH—(CH$_2$)—COO—alkyl where alkyl is from 1 to 4 carbon atoms and is straight or branched;

—SO$_2$NR$_7$R$_8$ where R$_7$ and R$_8$ are as defined above;

—SO$_2$OR$_9$ where R$_9$ is as defined above, or

—NH—SO$_2$R$_{10}$ where R$_{10}$ is alkyl of 1 to 4 carbon atoms or phenyl;

a N-oxide or (d) the group

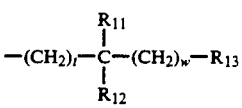

wherein t, w, R$_{11}$, R$_{12}$, and R$_{13}$ have the meanings defined hereinabove; or (e) 9-fluorenyl, 9-fluorenyl monosubstituted or disubstituted with chlorine, bromine, or fluorine, or 9-fluorenyl mono-substituted on the 1-, 2-, or 4-position with a straight or branched alkyl group having from 1 to 6 carbon atoms, straight or branched alkoxy having from 1 to 6 carbon atoms, hydroxy, hydroxymethyl, —COOH, —COOalkyl wherein the alkyl group is straight or branched and has from 1 to 6 carbon atoms, or —CONR$_5$R$_6$ wherein R$_5$ and R$_6$ have the meanings defined above;

R$_4$ is (a) hydrogen;

(b) a straight or branched hydrocarbon chain having from 1 to 20 carbon atoms and which is saturated or contains from 1 to 3 double bonds;

(c) the group

—(CH$_2$)$_t$—C(R$_{11}$)(R$_{12}$)—(CH$_2$)$_w$—R$_{13}$

Wherein t, w, R$_{11}$, R$_{12}$, and R$_{13}$ have the meanings defined hereinabove;

(d) —SO$_2$R$_{14}$ wherein R$_{14}$ is morpholino, phenyl or phenyl substituted with straight or branched alkyl having from 1 to 4 carbon atoms, or R$_{14}$ is a straight or branched hydrocarbon chain having from 1 to 20 carbon atoms which is saturated or contains from 1 to 3 double bonds;

(e)

wherein $R_{15}$ is a straight or branched hydrocarbon chain having from 1 to 20 carbon atoms which is saturated or contains from 1 to 3 double bonds, phenyl$(CH_2)_x$— wherein x is zero to two and wherein the phenyl ring is unsubstituted or is substituted with from one to three substituents selected from straight or branched alkyl having from 1 to 4 carbon atoms, chlorine, bromine, fluorine, trifluoromethyl, $NR_5R_6$ wherein $R_5$ and $R_6$ have the meanings defined above, —$CH_2NR_5R_6$ wherein $R_5$ and $R_6$ have the meanings defined above, straight or branched alkoxy having from 1 to 4 carbon atoms, diphenylmethyl, nitro, —$(CH_2)_p$—$COOR_{20}$ wherein $R_{20}$ is hydrogen or straight or branched alkyl having from 1 to 4 carbon atoms, and p is zero, one, or two;

(f) —$CO_2R_{15}$ wherein $R_{15}$ has the meaning defined above;

(g) —$COR_{18}$ wherein $R_{18}$ is selected from the groups defined for $R_{15}$ or is straight or branched alkyl having from 1 to 10 carbon atoms and is substituted with from 1 to 7 halogen atoms selected from chlorine, fluorine, or bromine; 9-fluorenylmethylene; pyrrolidino; or the group:

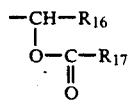

wherein $R_{16}$ is phenyl or phenyl substituted with one or two groups selected from straight or branched alkyl having from 1 to 4 carbon atoms, fluorine, chlorine or bromine, and $R_{17}$ is straight or branched lower alkyl having from 1 to 4 carbon atoms;

(h)

wherein $R_{15}$ has the meaning defined above;

(i) or $R_3$ is hydrogen or a saturated straight hydrocarbon chain having from 1 to 4 carbon atoms and $R_4$ is trityl;

(j) 9-fluorenyl or 9-fluorenyl substituted with from 1 to 3 substituents selected from fluorine, chlorine, bromine, straight or branched alkyl having from 1 to 4 carbon atoms, —NHCOalkyl or —$CO_2$ alkyl wherein alkyl is straight or branched and has from 1 to 4 carbon atoms;

(k) phenyl or phenyl substituted with one or two substituents selected from straight or branched alkyl having from 1 to 4 carbon atoms, chlorine, bromine, fluorine, trifluoromethyl, hydroxy, straight or branched alkoxy having from 1 to 4 carbon atoms, amino or nitro; or (l) —$(CH_2)_p$—$COOR_{20}$ wherein p and $R_{20}$ have the meanings defined above;

or pharmaceutically acceptable salts thereof, with the proviso that each of $R_1$, $R_2$, $R_3$, and $R_4$ are not hydrogen at the same time; each of $R_2$, $R_3$, and $R_4$ is not at the same time a straight or branched hydrocarbon chain having from 1 to 20 carbon atoms and which is saturated or contains 1 to 3 double bonds; when each of $R_2$, $R_3$, and $R_4$ represents the group

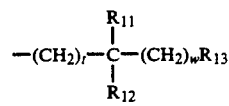

$R_{12}$ does not have the same meaning as $R_{13}$; and $R_{12}$ and $R_{13}$ are not a 9-fluorenyl substituent at the same time.

This invention also provides pharmaceutical compositions containing the compounds of Formula I and methods of treating hypercholesterolemia and atherosclerosis using the compounds of Formula I. The compounds of Formula I wherein $R_3$ and $R_4$ are both hydrogen are useful as intermediates in preparing pharmaceutically useful compounds of the invention. All the other compounds of Formula I are ACAT inhibitors.

DETAILED DESCRIPTION OF INVENTION

The compounds of the present invention as represented by Formula I provide a novel class of N,N'-disubstituted amino acid amide compounds which are ACAT inhibitors rendering them useful in treating hypercholesterolemia and atherosclerosis. Additionally N-[2,6-bis(1-methylethyl)phenyl]-2-bromopropanamide, N-[2,6-bis(1-methylethyl)phenyl]-2-bromo-2-phenylacetamide, and N-[2,6-bis(1-methylethyl) phenyl]-2-bromoacetamide in addition to being useful as intermediates to prepare compounds of Formula I are useful as ACAT inhibitors and are a part of the present invention.

Illustrative examples of straight or branched saturated alkyl groups having from 1 to 20 carbon atoms include methyl, ethyl, n-propyl, isopropyl, n-butyl, isobutyl, tert-butyl, n-pentyl, isopentyl, n-hexyl, n-heptyl, n-octyl, n-undecyl, n-dodecyl, n-hexadecyl, 2,2-dimethyldodecyl, 2-ethyltetradecyl, and n-octadecyl groups.

Illustrative straight or branched alkyl groups having from 1 to 20 carbon atoms and having from 1 to 3 double bonds are ethenyl, 2-propenyl, 2-butenyl, 3-pentenyl, 2-octenyl, 5-nonenyl, 4-undecenyl, 5-hepadecenyl, 3-octadecenyl, 9-octadecenyl, 2,2-dimethyl-11-eicosenyl, 9,12-octadecadienyl, and hexadecenyl.

Straight or branched alkoxy groups having from 1 to 6 carbon atoms include, for example, methoxy, ethoxy, n-propoxy, t-butoxy, and pentyloxy.

The group p-phenylmethoxybenzyl has the structure:

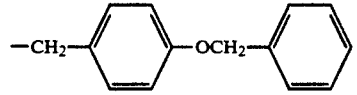

The group

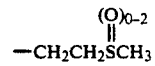

represents the sulfide derivative as well as the sulfone and sulfoxide and can be further illustrated as follows:
—CH$_2$CH$_2$SCH$_3$,

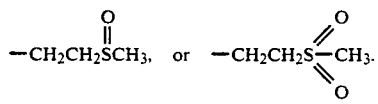

The group R may represent the group phenyl—(CH$_2$)$_n$ — wherein n is zero, one, or two wherein the phenyl moiety is unsubstituted or substituted. In other words R may represent phenyl, benzyl, or phenylethyl wherein the phenyl ring or phenyl moiety is substituted on any positions two through six or is unsubstituted.

The —NR$_5$R$_6$ substituent defined herein is amino, that is each of R$_5$ and R$_6$ is hydrogen or is a secondary amine when one of R$_5$ and R$_6$ represents hydrogen and the other represents lower alkyl or is a tertiary amine when each of R$_5$ and R$_6$ represents a lower alkyl group. Illustrative examples of lower alkyl groups which R$_5$ and R$_6$ may represent are methyl, ethyl, and n-propyl.

Illustrative examples of straight or branched alkyl groups having from 1 to 6 carbon atoms as used herein are methyl, ethyl, n-propyl, isopropyl, n-butyl, tert-butyl, n-pentyl and n-hexyl.

When the substituent group R$_{13}$ is a substituted phenyl group the phenyl ring may be substituted in any of positions two or six.

The group 9-fluorenyl as used herein means a substituent of the following structure being attached through the 9-position:

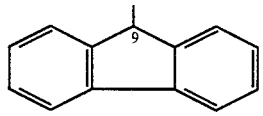

The group 9-fluorenylmethylene as used herein means a substituent of the following structure:

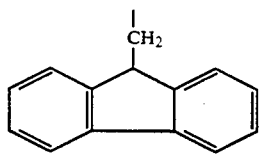

The substituent groups R$_{12}$ and R$_{13}$ may represent an aromatic monocyclic heterocyclic group having from 1 to 3 oxygen, sulfur, or nitrogen therein. Illustrative of such heterocyclic groups are the following: 2- or 3-thienyl; 2- or 3-furanyl; 2-, or 3-, or 4-pyridyl or -pyridyl-N-oxides; 2, 4, or 5-pyrimidinyl; 3- or 4-pyridazinyl; 2-pyrazinyl; 2- or 3-pyrrolyl; 3-, 4-, or 5-pyrazolyl, 3-, 4-, or 5-isoxazolyl; 3-, 4-, or 5-oxazolyl; 3-, 4-, or 5-isothiazolyl, 5-tetrazolyl; 3- or 5-(1,2,4-)triazolyl; 4- or 5-(1,2,3-)triazolyl; 2-, 4-, or 5-imidazolyl.

Preferred compounds of this invention are those wherein R is phenyl or substituted phenyl and more preferably phenyl substituted on the 2,6-positions. Other preferred compounds of this invention are those wherein R$_3$ represents the group

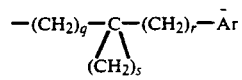

or the group

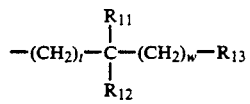

wherein q, r, s, Ar, t, w, R$_{11}$, R$_{12}$, and R$_{13}$ have the meanings defined in Formula I.

Pharmaceutically acceptable salts of the compounds of Formula I are also included as a part of the present invention.

The acid addition salts may be generated from the free base forms of the compounds by reaction of the latter with one equivalent of a suitable nontoxic, pharmaceutically acceptable acid, followed by evaporation of the solvent employed for the reaction and recrystallization of the salt, if required. The free base may be recovered from the acid addition salt by reaction of the salt with a water solution of the salt with a suitable base such as sodium carbonate, sodium bicarbonate, potassium carbonate, sodium hydroxide, and the like.

Suitable acids for forming acid addition salts of the compounds of this invention include, but are not necessarily limited to acetic, benzoic, benzenesulfonic, tartaric, hydrobromic, hydrochloric, citric, fumaric, gluconic, glucuronic, glutamic, lactic, malic, maleic, methanesulfonic, pamoic, salicylic, stearic, succinic, sulfuric, and tartaric acids. The class of acids suitable for the formation of nontoxic, pharmaceutically acceptable salts is well known to practitioners of the pharmaceutical formulation arts. (See, for example, Stephen N. Berge, et al. *J. Pharm. Sciences*, 66:1–19 (1977).

The compounds of the present invention may also exist in different stereoisomeric forms by virtue of the presence of one or more asymmetric centers in the compound. The present invention contemplates all stereoisomeric forms of the compounds as well as mixtures thereof, including racemic mixtures. Individual stereoisomers may be obtained, if desired by methods known in the art as, for example, the separation of stereoisomers in chiral chromatographic columns.

Further, the compounds of this invention may exist in unsolvated as well as solvated forms with pharmaceutically acceptable solvents such as water, ethanol and the like. In general, the solvated forms are considered equivalent to the unsolvated forms for the purposes of this invention.

As shown by the data presented below in Table 1, the compounds of the present invention are potent inhibitors of the enzyme acyl-CoA:cholesterol acyl-transferase (ACAT), and are thus effective in inhibiting the esterification and transport of cholesterol across the intestinal cell wall. The compounds of the present invention are thus useful in pharmaceutical formulations for the treatment of hypercholesterolemia or atherosclerosis.

The ability of representative compounds of the present invention to inhibit ACAT was measured using an in vitro test more fully described in Field, F. J. and Salone, R. G., *Biochemica et Biophysica* 712: 557–570 (1982). The test assesses the ability of a test compound to inhibit the acylation of cholesterol by oleic acid by measuring the amount of radio-labeled cholesterol oleate formed from radiolabeled oleic acid in a tissue preparation containing rabbit intestinal microsomes.

The data appear in Table 1 where they are expressed as $IC_{50}$ values; i.e. the concentration of test compound required to inhibit 50% expression of the enzyme.

TABLE 1

| Compound of Example | $IC_{50}$ ($\mu M$) |
| --- | --- |
| 4 | 0.055 |
| 10 | 0.10 |
| 21 | 1.05 |
| 41 | 0.35 |
| 52 | 0.96 |

In one in vivo screen, designated APCC, male Sprague-Dawley rats (200 to 225 g) were randomly divided into treatment groups and dosed at 4 PM with either vehicle (CMC/Tween) or suspensions of compounds in vehicle. The normal, chow diet was then replaced with the PCC diet (RR 740-02122) with either 1% or 0.5% cholic acid, as indicated. The rats consumed this diet ad libitum during the night and were sacrificed at 8 AM to obtain blood samples for cholesterol analysis using standard procedures (RR 740-02122). Statistical differences between mean cholesterol values for the same vehicle were determined using analysis of variance followed by Fisher's least significant test. The results of this trial for representative compounds of the present invention appear in Table 2.

TABLE 2

| Compound of Example | % Change (mg/dl) |
| --- | --- |
| 4 | −45 |
| 10 | −30 |
| 11 | −3 |
| 14 | −24 |

In therapeutic use as agents for treating hypercholesterolemia or atherosclerosis, the compounds of Formula I are administered to the patient at dosage levels of from 250 to 3000 mg per day. For a normal human adult of approximately 70 kg of body weight, this translates into a dosage of from 5 to 40 mg/kg of body weight per day. The specific dosages employed, however, may be varied depending upon the requirements of the patient, the severity of the condition being treated, and the activity of the compound being employed. The determination of optimum dosages for a particular situation is within the skill of the art.

For preparing pharmaceutical compositions from the compounds of this invention, inert, pharmaceutically acceptable carriers can be either solid or liquid. Solid form preparations include powders, tablets, dispersible granules, capsules, and cachets.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active compound is mixed with the carrier having the necessary binding properties in suitable proportions and compacted in the shape and size desired.

Powders and tablets preferably contain between about 5 to about 70% by weight of the active ingredient. Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The term "preparation" is intended to include the formulation of the active compound with encapsulating material as a carrier providing a capsule in which the active component (with or without other carriers) is surrounded by a carrier, which is thus in association with it. In a similar manner, cachets are also included.

Tablets, powders, cachets, and capsules can be used as solid dosage forms suitable for oral administration.

Liquid form preparations include solutions suitable for oral administration, or suspensions and emulsions suitable for oral administration. Aqueous solutions for oral administration can be prepared by dissolving the active compound in water and adding suitable flavorants, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethyl cellulose, and other suspending agents known to the pharmaceutical formulation art.

Preferably, the pharmaceutical preparation is in unit dosage form. In such form, the preparation is divided into unit doses containing appropriate quantities of the active component. The unit dosage form can be a packaged preparation, the package containing discrete quantities of the preparation, for example, packeted tablets, capsules, and powders in vials or ampoules. The unit dosage form can also be a capsule, cachet, or tablet itself, or it can be the appropriate number of any of these packaged forms.

The compounds of this invention can be prepared in various ways, all of which are well known in the art. In referring to Chart I, Scheme I, the compounds can be prepared by reacting a α-haloacyl halide (1) with an amine (2) in acetonitrile or a nonpolar aprotic solvent such as THF, ethyl acetate, diethyl ether, dichloromethane, or dioxane for from about 5 minutes to about 2 hours at a temperature varying from about −78° to room temperature. To the resulting amide (3) is added the amine (4) and the reaction is allowed to proceed for from about 1 hour to 3 days at from about 0° C. to 100° C., depending on the amine (4) employed. One may also remove the solvent from the amide (3) and combine the amide (3) and the amine (4) in DMF and heat the reaction to boiling, each procedure giving compounds of Formula I wherein $R_4$ is hydrogen (5). The compounds of (5) may be alkylated or acylated to give other compounds of Formula I as represented by (6) by procedures well known in the art. The reaction time may vary from a few minutes to several days depending on the acylating or alkylating reagent employed. The reactions may be carried out in any aprotic nonpolar solvent. The alkylation reaction may also be carried out in DMF with heating.

The compounds of this invention may also be prepared by the procedure outlined in Scheme 2 of Chart 1 whereby an appropriate amino acid (7) is protected with, e.g., t-butoxy-carbonyl or benzyloxycarbonyl by treatment with (t-butylO$_2$C)$_2$O or benzylchloroformate. The reaction may be carried out in e.g., triethylamine, THF and sodium bicarbonate, dioxane and water for from 1 to 24 hours at a temperature of from about 0° C.

to room temperature to give the protected amine (8). The protected amine (8) is then treated with a haloformate of the formula halo-COOR$_{20}$ wherein R$_{20}$ is, e.g., isobutyl for from 1 to 3 hours at from about −40° to 0° C. in solvents such as THF, dichloromethane, ethyl acetate or diethyl ether, after which an amine of the formula RNH$_2$ is added and the reaction is permitted to proceed for from about 1 to 72 hours to give the amide (9). The amide is deprotected using, e.g., by using mineral acid or trifluoroacetic acid or by hydrogenolysis or HBr in acetic acid to give the free amine (10). The amide may also be deprotected using HCl gas and methylene chloride at 0° C. The amine is alkylated and acylated as generally described above to give compounds of Formula I. The alkylation may also be achieved by reductive amination.

In Chart I the symbols R, R$_1$, R$_2$, R$_3$, and R$_4$ have the meanings defined in Formula I and halo is chlorine or bromine, and B is t-butyl or benzyl.

The compounds represented in Scheme 1 as formula (5) may also be prepared by heating a mixture of the amine (10) in Scheme 2 and a suitable carbamyl compound $$X-\overset{O}{\underset{\|}{C}}-Y$$

wherein X-CH-Y is R$_3$) in an inert solvent such as toluene heating to reflux in the presence of a catalyst such as hydrogen chloride and removing the generated water with a Dean Stark trap.

In Scheme 1 in Chart I when R$_3$ in the amine H$_2$NR$_3$ is hindered and/or R$_1$ and R$_2$ in compounds of formula (3) are other than hydrogen forcing conditions such as high temperatures and long reaction times may be required to effect the displacement of the halo with R$_3$NH$_2$.

Compounds of this invention wherein R$_2$ represents —CH$_2$CH$_2$S(O)0—2—CH$_3$ and R$_2$ is the sulfone or sulfoxide derivative are prepared by treating the corresponding sulfide compound with a stoichiometric amount of an oxidizing agent such as meta-chloroperbenzoic acid in an inert solvent such as dichloromethane for 1 to 36 hours.

In Scheme 2 the amino acids (7) wherein R$_1$ is hydrogen can be synthesized by reacting a malonic acid derivative [AcNHCH(CO$_2$C$_2$H$_5$)$_2$] with an alkyl halide (R$_2$ halo) in the presence of a suitable base such as sodium ethoxide. Acid (6N HCl) or base (5N NaOH) catalyzed hydrolysis can be employed to give the amino acid (7).

The benzhydrylamines which compounds (2) and (4) may represent are commercially available or may be prepared by procedures well known in the art, for example, by reduction of the corresponding benzophenone oxime or by condensation of an appropriate benzhydrol with benzyl carbamate in an acidic media followed by alkaline hydrolysis. The preparation of benzophenones is well known in the art, see, e.g., the review by D. A. Walsh, *Synthesis*, 1980, 677.

The heterocyclic phenones required for the synthesis of the heterocyclic analogues of the benzhydryl amines may be prepared as outlined for the benzophenones by D. A. Walsh, *Synthesis* 1980, 677. Alternative methods may also be employed to synthesize the required heterocyclic amines (e.g., from suitably protected phenylglycinonitriles by methods outlined by Meyers and Sircar "Addition to the Cyano Group to form Heterocycles," in the Chemistry of the Cyano Group, Ed. Z. Rappoport, J. Wiley and Sons, New York, p. 341 (1970).

In Scheme 1 of Chart I the amines (4) wherein R$_3$ represents the group

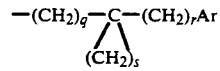

are prepared as set forth in Chart II. The amines are prepared by the general method described in *J. Org. Chem.* 36(9), 1308 (1971). In referring to Chart II phenylacetonitrile or the appropriately substituted phenylacetonitrile is reacted with an alpha-omega dibromoalkane in the presence of base to produce the cycloalkylnitrile (13). The cycloalkylnitrile can be catalytically reduced using hydrogen over a noble metal catalyst to give the aryl (aminomethyl)cycloalkane (14). Also, the cycloalkylnitrile can be acid hydrolyzed to the corresponding amide (15) which is converted to the amine (16) via a Hofmann degradation.

EXAMPLE 1

(±)-N-[2,6-bis(1-Methylethyl)phenyl]-2-bromopropanamide

A solution of (±) 2-bromopropionyl bromide (2.16 g, 10 mmol) in CH$_2$Cl$_2$ (5 mL) was added to a well stirred ice-cold solution of 2,6 diisopropyl aniline (1.77 g, 10 mmol) in CH$_2$Cl$_2$ (25 mL) containing Et$_3$N (1.1 g, 10 mmol). The ice-bath was removed after 30 minutes, and the reaction mixture was stirred at room temperature for 16 hours followed by heating under reflux for 2 hours. It was diluted with CH$_2$Cl$_2$ (25 mL), and the solution was washed with water, dried over anhydrous MgSO$_4$, and evaporated to yield 3.5 g of a soft solid. It was triturated with hexane and filtered to give 2.2 g (70%) of a white solid. $^1$H NMR was consistent with the title compound. By substituting chloroacetyl chloride in place of 2-bromopropionyl bromide in the above experiment 2.3 g (90%) of (±)-N-[2,6-bis(1-Methylethyl)phenyl]-2-chloroacetanilide derivative was obtained. Similarly by substituting (±) 2-bromohexanoyl bromide in place of 2-bromopropionyl bromide in the above experiment 2.8 g (79%) of (±)-N-[2,6-bis(1-Methylethyl)phenyl]-2-bromohexaneamide derivative was obtained.

EXAMPLE 2

(±)-N-[2,6-bis(1-Methylethyl)phenyl]2-[[(1-phenyl cyclopentyl)methyl]amino]propanamide A mixture of 1.1 g (3.5 mmol) of (±)-N-[2,6-bis(1-Methylethyl)phenyl]-2-bromopropanamide, 0.62 g (3.5 mmol) of 1-phenyl cyclopentyl amine and 0.4 g (4.0 mmol) of Et$_3$N in CH$_3$CN (20 mL) was heated under reflux for 18 hour. The solution was evaporated, and the residue was dissolved in EtOAc. The solution was washed with water, dried over anhydrous MgSO$_4$ and stripped to yield a solid which was purified via chromatography (SiO$_2$, CH$_2$Cl$_2$/CH$_3$OH (10%) to give 0.3 g (21%) of the desired material.

Analyzed for C$_{27}$H$_{38}$N$_2$0.0.2 H$_2$1O: Calcd: C, 79.10; H, 9.34; N, 6.83. Found: C, 79.00; H, 9.4%; N, 6.63

Similarly, by using (±)-N-[2,6-bis(1-Methylethyl)-phenyl]-2-bromohexaneamide in the above procedure. (±)-N-2,6-bis(1-Methylethyl)phenyl]-2-[[(1-phenylcyclopentyl)methyl]amino] hexanamide was obtained in 52% yield.

Analyzed for $C_{30}H_{44}N_2O$: Calcd: C, 80.35; H, 9.82; N, 6.25. Found: C, 80.13; H, 9.85; N, 6.02.

EXAMPLE 3

(±)-N-[2,6-bis(1-Methylethyl)phenyl]-α-[(4-morpholinylsulfonyl)amino]benzenepropanamide 2.0 g (6.36 mmol) of the N-morpholinosulfonylphenylaniline was added to ice-cold $SOCl_2$ (4 mL), and the reaction mixture was gradually warmed to room temperature and stirred overnight at room temperature. The solvent was evaporated under rotary evaporator. Toluene (10 mL) was added and the solution was evaporated. This process was repeated twice to remove any excess HCl(g). This was dissolved in THF (20 mL) and added slowly to a solution of 2,6-diisopropylaniline (1.0 g, 5.72 mmol) and $Et_3N$ (1.3 mL, 12.7 mmol) in THF (20 mL). The solution was stirred overnight at room temperature to complete the reaction. THF was evaporated, the residue was dissolved in $CH_2Cl_2$, and the solution was washed successively with 1N HCl, saturated $NaHCO_3$, and brine. The solution was dried over anhydrous $MgSO_4$, stripped and chromatographed ($SiO_2$, 0–2% $MeOH/CHCl_3$) to give 3 g (85%) of the desired product.

Anal for $C_{25}H_{35}N_3O_4S$. 0.45 $CHCl_3$: Calcd: C, 57.96; H, 6.77; N, 7.97. Found: C, 58.01; H, 6.75; N, 7.91.

Mass spectrum indicate molecular ion peak at 473. $[\alpha]_D^{23} = -41.23$ (c=0.65% $CHCl_3$).

EXAMPLE 4

N-[2,6-bis(1-Methylethyl)phenyl]-2-[(diphenylmethyl)amino]acetamide

Bromoacetylbromide (4.5 mL) was added dropwise to a solution of 8.85 g 2,6-diisopropylaniline and 7.0 mL triethylamine in 200 mL. EtoAc at 0° C. After stirring 10 minutes at 0° C., 9.15 g aminodiphenylmethane and 10 mL triethylamine were added and the resulting mixture was removed from the cooling bath and heated on the steambath for thirty minutes. The reaction mixture was allowed to sit overnight at room temperature. The mixture was filtered, heated an additional 30 minutes on the steambath, filtered again and concentrated to a brown oil/solid. This oil/solid was triturated with a solution of hexane/EtoAc, 1/1, and the insoluble material collected by filtration. The resulting solid was then filtered through $SiO_2$ (70–230 mesh) using EtoAc as eluant. Concentration of the appropriate fractions yielded the product 5.65 g, as a white solid. Concentration and silica gel filtration of the mother liquors yielded an additional 4.45 g of product. Total yield, 10.1 g (50.5%). NMR ($CDCl_3$) δ 1.20 (12H, d), δ 3.04 (2H, m), δ 3.50 (2H, s), δ 4.96 (1H, s), δ 7.08–7.43 (13H, m), δ 8.61 (1H, s) IR (KBr) 3236, 2965, 1656, 1540, 1493, 1453, 1385, 766, 701 cm$^{-1}$.

EXAMPLE 5

N-[2,6-bis(1-Methylethyl)phenyl]-2-[(1,1-dimethyl-2-phenylethyl)amino]acetamide

The title compound was prepared according to the procedure for Example 1 by substituting 1,1-dimethyl-2-phenylethyl amine for benzhydrylamine. 9.93 g, (54.2%). NMR($CDCl_3$) δ 1.18 (18H, s, d), δ 2.74 (2H, s), δ 3.01 (2H, m), δ 3.48 (2H, s), δ 7.15–7.34 (8H, m), δ 8.91 (1H, bs). IR (KBr) 3277, 2961, 2930, 2919, 1659, 1497, 1458, 744, 724 cm$^{-1}$.

EXAMPLE 6

N-[2,6-bis(1-Methylethyl)phenyl]-2-[[(1-phenylcyclopentyl)methyl]amino]acetamide The title compound was prepared according to the procedure for Example 1 by substituting phenylcyclopentylmethylamine for benzhydrylamine. 2.28 g, (58.2%). NMR ($CDCl_3$) δ 1.18 (12H, d), δ 1.71 (4H, m), δ 1.98 (4H, m), δ 2.84 (2H, s), δ 2.91 (2H, m), δ 3.30 (2H, s), δ 7.14–7.35 (8H, m), δ 8.47 (1H, bs). IR (film) 3294, 2960, 1683, 1505, 1496, 796, 749, 701 cm$^{-1}$.

EXAMPLE 7

(Z)-2-(9-Octadecenylamino)-N-(2,4,6-trimethoxyphenyl)acetamide

The title compound was prepared according to the procedure for Example 1 by substituting oleyl amine for benzhydryl amine and 2,4,6-trimethoxy aniline for 2,6-diisopropyl aniline. 11.45 g (58%). NMR ($CDCl_3$) δ 0.88 (3H, t), δ 1.2–1.52 (24H, m), δ 2.01 (4H, m), δ 2.71 (2H, t), δ 3.42 (2H, m), δ 3.68 (3H, s), δ 3.79 (6H, s), δ 5.33 (2H, m), δ 6.13, (2H, d), δ 8.31 (1H, bs) IR (film) 3310, 3003, 2928, 1669, 1346, 1062, 954, 811 cm$^{-1}$.

EXAMPLE 8

(Z)-N-(2,6-Dimethylphenyl)-2-(9-octadecenylamino)acetamide

The title compound was prepared according to the procedure for Example 1 by substituting oleyl amine for benzhydryl amine and 2,6-dimethyl aniline for 2,6-diisopropyl aniline. 11.2 g (65%). NMR ($CDCl_3$) δ 0.88 (3H, t), δ 1.24–1.73 (24H, m), δ 1.98 (4H, m), δ 2.23 (6H, s), δ 2.72 (2H, t), δ 3.43 (2H, s), δ 5.34 (2H, m), δ 7.06 (3H, s), δ 8/82 (1H, bs). IR (film) 2925, 2855, 1665, 1504, 1468, 1377, 768, 724 cm$^{-1}$.

EXAMPLE 9

N-[2,6-bis(1-Methylethyl)phenyl]-2-[(diphenylmethyl)amino]acetamide

The title compound was prepared according to the procedure for Example 1 by substituting 2-phenylethylamine for benzhydryl amine. 14.8 g (88%). NMR ($CDCl_3$) δ 1.19 (12H, d), δ 1.68 (1H, bs), δ 2.87 (2H, t), 3.01 (4H, m), δ 3.45 (2H, s), δ 7.10–7.34 (8H, m), δ 8.66 (1H, bs). IR (KBr) 3224, 2965, 1653, 1529, 1453, 700 cm$^{-1}$.

EXAMPLE 10

N-[2,6-bis(1-Methylethyl)phenyl]-2-[[(phenylamino)thioxomethyl][(1-phenylcyclopentyl)methyl]amino]acetamide Phenylisothiocyanate (0.103 g) was added to the product of Example 6 in a few mL ethyl acetate at room temperature. This mixture was allowed to sit 4 days at room temperature, concentrated, and the resulting solid collected by filtration from a slurry in hexane. 0.31 g (84%). NMR ($CDCl_3$) δ 1.21 (12H, d), δ 1.74–2.14 (8H, m), δ 3.08 (2H, m), δ 3.89 (2H, s), δ 4.92 (2H, bs), δ 618 (1H, s), δ 6.67 (2H, d), δ 7.06–7.51 (11H, m), δ 8.88 (1H, s). IR (KBr) 2963, 2871, 1668, 1600, 1518, 1499, 1350, 1204, 703 cm$^{-1}$.

EXAMPLE 11

N-(2,6-bis(1-Methylethyl)phenyl]-2-[[(phenylamino)-carbonyl][(1-phenylcyclopentyl)methyl]amino]-acetamide Phenylisocyanate (0.092 g) was added to a solution of the product of Example 6 (0.250 g) in a few mL ethyl acetate at room temperature. The reaction mixture was allowed to sit 4 days at room temperature, concentrated, and the resulting white solid collected by filtration from a slurry in hexane. 0.30 g (94%). NMR (CDCl$_3$) δ 1.14 (12H, d), δ 1.59-2.10 (8H, m), δ 3.04 (2H, m), δ 3.61 (2H, s), δ 4.12 (2H, bs), δ 5.55 (1H, s), δ 6.77-7.51 (13H, m), δ 8.26 (1H, bs). IR (KBr) 2963, 2871, 1668, 1599, 1534, 1501, 1446, 1312, 1240, 703 cm$^{-1}$.

EXAMPLE 12

N-[2,6-bis(1-Methylethyl)phenyl]-2-[[[(2,4-difluorophenyl)amino]carbonyl][(1-phenylcyclopentyl)methyl]amino]acetamide The title compound was prepared according to the procedure for Example 11 by substituting 2,4-difluorophenylisocyanate for phenyl isocyanate. 0.37 g (97%) NMR (CDCl$_3$) δ 1.12 (12H, d), δ 1.58-2.10 (8H, m), δ 2.96 (2H, m), δ 3.63 (2H, s), δ 3.97 (2H, s), δ 5.83 (1H, bs), δ 6.70-7.49 (11H, m), δ 7.85 (1H, bs). IR (KBr) 2964, 2872, 1666, 1518, 1432, 1258, 1142, 968, 704 cm$^{-1}$.

EXAMPLE 13

N-[2,6-bis(1-Methylethyl)phenyl]-2-[[[[2,6-bis(1-methylethyl)phenyl]amino]carbonyl][(1-phenylcyclopentyl)methyl]amino]acetamide 2,6-Diisopropylphenylisocyanate (0.24 g) and the product of Example 6 (0.45 g) were mixed and then diluted with a few mL of ethyl acetate. The solution was heated on the steambath and then concentrated to an oil which was heated on the steambath. Upon cooling to room temperature the oil partially solidified. Addition of hexane/EtOAc, 1/1 caused crystallization of the product which was collected by filtration. 0.30 g (44%). NMR (CDCl$_3$) δ 1.08 (12H ,d), δ 1.17 (12H, d), δ 1.60-2.13 (8H, m), δ 2.65 (2H, m), δ 3.04 (2H, m), δ 3.71 (2H, s), δ 4.04 (2H, bs), δ 5.24 (1H, bs), δ 7.04-7.48 (11H, m), δ 7.94 (1H, bs). IR (KBr) 3025, 2965, 2871, 1682, 1637, 1519, 1364, 1230, 958, 801, 700 cm$^{-1}$.

EXAMPLE 14

N-[2,6-bis(1-Methylethyl)phenyl]-2-[[(4-methylphenyl)sulfonyl][(1-phenylcyclopentyl)methyl]amino]acetamide To a mixture of the product of Example 6 (0.45 g) and excess triethylamine at room temperature was added 0.22 g p-toluene sulfonyl chloride. This mixture was diluted with ethyl acetate, concentrated, and triethylamine and ethyl acetate added a second time. The reaction mixture was then concentrated to a brown oil. After sitting 5 days at room temperature, the oil was taken up in ethyl acetate, washed with NaHCO$_3$ and NaCl solutions, dried over MgSO$_4$, filtered, and concentrated to an oil. The oil was purified by chromatography on silica gel using hexane/EtOAc, 8/21 as eluant. The appropriate fractions were concentrated to an oil which crystallized upon trituration with hexane. 0.44 g (69%). NMR (CDCl$_3$) δ 1.17 (6H, d), δ 1.64-1.82 (4H, m), δ 2.03 (4H, m), δ 2.42 (3H, s), δ 2.97 (2H, m), δ 3.42 (2H, s), δ 3.55 (2H, s), δ 7.13-7.65 (12H, m). IR (KBr) 3370, 2965, 2870, 1673, 1497, 1328, 1158, 1092, 755, 550 cm$^{-1}$.

EXAMPLE 15

N-[2-[[2,6-bis(1-Methylethyl)phenyl]amino]-2-oxoethyl]-N-[(1-phenylcyclopentyl)methyl]benzamide To a solution of 0.48 g of the product of Example 6 and excess triethylamine in ethyl acetate at room temperature was added 0.16 mL benzoyl chloride all at once. The reaction mixture was allowed to sit 4 days at room temperature. The solution was then diluted with ethyl acetate and washed with dilute HCl, NaHCO$_3$, and NaCl solutions, dried over MgSO$_4$, filtered, and concentrated to an oil which was crystallized from diethyl ether. The white solid was collected by filtration. 0.48 g (61%). NMR (CDCl$_3$) δ 1.12 (12H, d), δ 1.6-2.15 (8H, m), δ 2.99 (2H, m), δ 3.27 (2H, bs), δ 3.80 (2H, bs), δ 6.20 (1H, bs) δ 7.04-7.42 (13H, m). IR (KBr) 3269, 2963, 2869, 1696, 1600, 1520, 1461, 1254, 1222, 703 cm$^{-1}$.

EXAMPLE 16

(Z)-2-(9-Octadecenyl)(phenylmethyl)amino]-N-(2,4,6-trimethoxyphenyl)acetamide

To a mixture of 0.50 g of the product of Example 7 and 0.3 g benzylbromide was added excess triethylamine and ethyl acetate. The mixture was heated on the steambath and then allowed to sit 3 days at room temperature. The reaction mixture was washed with NaHCO$_3$ and NaCl solutions, the organic layer dried over MgSO$_4$, filtered, and concentrated. The residue was chromatographed on SiO$_2$ (70–230 mesh) using hexane/EtOAc, 1/1, as eluant. Combination of the appropriate fractions and concentration yielded the product as a light yellow oil. 0.91 g (32%). NMR (CDCl$_3$) δ 0.88 (3H, t), δ 1.25 (24H, m), δ 1.55 (2H, m), δ 1.97 (4H, m), δ 2.54 (2H, m), δ 3.23 (2H, s), δ 3.73 (9H, m), δ 5.32 (2H, m), δ 6.15 (2H, s), δ 7.25-7.38 (5H, m), δ 8.38 (1H, bs). IR (film) 3353, 2925, 1599, 1517, 1466, 1206, 1131, 699 cm$^{-1}$.

EXAMPLE 17

(Z)-2-[9-Octadecenyl[[(2-phenylethyl)amino]carbonyl]amino]-N-(2,4,6-trimethoxyphenyl)acetamide A mixture of 0.50 g of the product of Example 7, 0.2 g 2-phenethyl isocyanate, and a few mL ethyl acetate were briefly heated on the steambath and then allowed to sit 3 days at room temperature. The reaction mixture was then washed with dilute H$_3$PO$_4$, NaHCO$_3$, and HaCl solutions, dried over MgSO$_4$, filtered, and concentrated to an oil. The oil was chromatographed on SiO$_2$ (70–230 mesh) using EtoAc as eluant. The product was obtained as an oil which crystallized on standing. 0.28 g (44%). NMR (CDCl$_3$) δ 0.88 (3H, t), δ 1.25 (24H, m), δ 1.96 (4H, m) δ 2.84 (2H, t), δ 3.23 (2H, t), δ 3.51 (2H, q), δ 3.69 (6H, s), δ 3.77 (3H, s), δ 4.03 (2H, s), δ 4.70 (1H, t), δ 5.35 (2H, t), δ 6.13 (2H, s), δ 7.16-7.31 (5H, m), δ 7.46 (1H, s). IR (KBr) 3251, 2925, 1662, 1621, 1533, 1465, 1156, 1128, 810 cm$^{-1}$.

EXAMPLE 18

(Z)-[[[[2,6-bis(1-Methylethyl)phenyl]amino]carbonyl]-9-octadecenylamino]-N-[2,4,6-trimethoxyphenyl)acetamide A mixture of 0.50 g of the product of Example 7, 0.22 g 2,6-diisopropylphenylisocyanate and a few mL ethyl acetate was allowed to sit 3 days at room temperature. The solvent was removed and the residue chromatographed on SiO$_2$ (70-230 mesh) using hexane/EtOAc, 1/1, as eluant. The product was obtained as a white solid. 0.33 g (46%). NMR (CDCl$_3$) δ 0.88 (3H, t), δ 1.15 (12H, d), δ 1.21-1.26 (22H, m) δ 1.78 (2H, m), δ 2.02 (4H, m), δ 3.10 (2H, m), δ 3.47 (2H, t), δ 3.75 (6H, s), δ 3.80 (3H, s), δ 4.17 (2H, s), δ 5.35 (2H, t), δ 6.07 (1H, s), δ 6.14 (2H, s), δ 7.13-7.25 (3H, m), δ 7.72 (1H, s). IR (KBr) 3242, 2959, 2525, 1675, 1627, 1508, 1156, 1135 cm$^{-1}$.

EXAMPLE 19

(Z)-2-[[(4-Methylphenyl)sulfonyl](9-octadecenyl)amino]-N-(2,4,6-trimethoxyphenyl)acetamide To a mixture of 0.50 g of the product of Example 7, excess triethylamine, and ethyl acetate at room temperature was added 0.25 g p-toluene sulfonyl chloride and this was allowed to sit 3 days at room temperature. The reaction mixture was then washed with H$_3$PO$_4$, NaHCO$_3$, and NaCl solutions, dried over MgSO$_4$, filtered, and stripped to an oil. This oil was purified by chromatography on silica gel (70-230 mesh) using 1/1 hexane/EtOAc as eluant. The product was obtained as a viscous oil. 0.28 g (42%). NMR (CDCl$_3$) δ 0.88 (3H, z), δ 1.26 (24H, m), δ 1.66 (2H, m), δ 2.01 (4H, m), δ 2.44 (3H, s), δ 3.21 (2H, m), δ 3.79-3.88 (9H, m), δ 5.34 (2H, m), δ 6.15 (2H, s), δ 7.26-7.75 (5H, m). IR (KBr) 3019, 2925, 1599, 1466, 1206 cm$^{-1}$.

EXAMPLE 20

(S)-1,1-Dimethylethyl[2-[[2,6-bis-(1-methylethyl)phenyl]amino]-2-oxo-1-[[4-(phenylmethoxy)phenyl]methyl]ethyl]carbamate Triethylamine (4.13 mL, 29.6 mmol) was added to a cooled (−10° C.) solution of N-boc-O-benzyl-(L)-tyrosine (10.0 g, 26.9 mmol) in THF (130 mL). The resulting solution was stirred (15 min, −10° C.), then 2,6-diisopropylaniline (5.59 mL, 29.6 mmol) was added in one portion. The resulting slurry was warmed to room temperature, stirred (16 hours, 25° ), then filtered. The filtrate was concentrated in vacuo, and the residue was taken up in ethyl acetate (300 mL). The ethyl acetate layer was washed with water (1×100 mL) with saturated aqueous sodium bicarbonate (1×100 mL), with brine (1×100 mL), then dried (MgSO$_4$) and concentrated. The resulting solid was washed with cold ether:-hexane (1:1), collected by filtration, and dried in a vacuum oven at 45° C. to yield 8.8 g (61.5%) of the title compound as a white solid.

Anal for C$_{33}$H$_{42}$N$_2$O$_4$: Calcd: C, 74.69; H, 7.98; N, 5.28. Found: C, 74.48; H, 7.91; N, 5.06.

$^1$H NMR (CDCl$_3$): δ 7.45-7.20 (m, 8H), 7.11 (d, 2H, J=8.1 Hz), 6.93 (d, 2H, J=8.1 Hz), 5.14 (br d, 1H, J=8.1 Hz), 0.04 (s, 2H), 4.53 (q, 1H, J=7.4 Hz), 3.11 (m, 2H), 2.76 (m, 2H), 1.46 (s, 9H), and 1.08 (apparent t, 12H). IR: principle absorptions at 3400, 2870, 1695, 1650, 1250, and 1150 cm$^{-1}$. Melting point: 144°-150° C.

EXAMPLE 21

(S)-1,1-Dimethylethyl[2-[[2,6-bis-(1-methylethyl)-phenyl]amino]-1-[(4-hydroxyphenyl)-methyl]-2-oxoethyl]carbamate Palladium on activated charcoal (0.2 g, 20%) was added in one portion to a solution of (S)-1,1-dimethylethyl[2-[[2,6-bis(1-Methylethyl)phenyl]amino)-2-oxo-1-[[4-(phenylmethoxy)phenyl]methyl]ethyl]carbamate (1.0 g, 1.9 mmol) in methanol (100 mL) under a nitrogen atmosphere. The nitrogen was evacuated and 50 PSI of hydrogen was introduced. After vigorous shaking (22 hours, 25° C.) the resulting suspension was filtered and the filtrate concentrated in vacuo to yield 0.73 g (88.0%) of the title compound as a solid foam. $^1$H NMR (CDCl$_3$): δ 7.37 (s, 1H), 7.26 (t, 1H, J=7.7 Hz), 7.12 (overlapping d, 2H, d, 2H), 5.86 (br s, 1H), 5.12 (br d, 1H), 4.51 (q, 1H, J=8.0 Hz), 3.09 (m, 2H), 2.77 (m, 2H), 1.68 (br s, 1H), 1.47 (s, 9H), and 1.08 (apparent t, 12H). IR: Principle absorptions at 3300, 2950, 1670, 1520, 1250, and 1170 cm$^{-1}$. Melting point: 92°-107° C.

EXAMPLE 22

(S)-α-Amino-N-[2,6-bis(1-methylethyl)-phenyl]4-(phenylmethoxy)benzenepropanamide Hydrogen chloride gas was bubbled through a cooled (0° C.) solution of (S)-1,1-dimethylethyl[2-[[2,6-bis(1-Methylethyl)phenyl]amino]-2-oxo-1-[4-(phenylmethoxy)phenyl]methyl]ethyl]carbamate (6.0 g, 11.3 mmol) in dichloromethane (100 mL) for 5 minutes. The resulting solution was stirred (1 hour, 0° C.), then an excess of solid sodium bicarbonate was added slowly. The resulting slurry was warmed to room temperature, stirred (20 minutes, 25° C.), then partitioned between dichloromethane (200 mL) and water (100 mL). The organic layer was washed with brine (1×100 mL), then dried and concentrated to an oil. Ether was added and the resulting solid was collected by filtration and washed with cold ether to yield 4.3 g (88.3%) of the title compound as a white powder. $^1$H NMR (CDCl$_3$): δ 8.83 (s, 1H), 7.46-7.10 (m, 10H), 6.95 (d, 2H, J=8.5 Hz), 5.06 (s, 2H), 3.79 (dd, 1H, J=9.2, 3.9 Hz), 3.28 (dd, 1H, J=13.8, 3.9 Hz), 2.97 (heptet, 2H, J=6.9 Hz), 2.86 (dd, 1H, J=13.8, 9.2 Hz), 1.63 (s, 2H), and 1.17 (d, 12H, J=6.9 Hz). IR: Principle absorptions at 3300, 2950, 1670, 1510, 1250, and 750 cm$^{-1}$. Melting point: 117°-122° C.

EXAMPLE 23

(S)-N-[2,6-bis(1-Methylethyl)phenyl]-α-[[[(1,1-dimethylethyl)amino]carbonyl]amino]-4-phenylmethoxy)-benzenepropanamide A solution of (S)-α-amino-N-[2,6-bis(1-Methylethyl)phenyl]-4-(phenylmethoxy)benzenepropanamide (1.4 g, 3.3 mmol) and tert-butylisocyanate (0.37 mL, 3.3 mmol) in ethyl acetate (100 mL) was stirred (16 hours, 25° C.). The resulting mixture was cooled (0° C.), and the solid (gel) was collected by filtration. The resulting solid was dried in a vacuum oven at 45° C. to yield 1.3 g (75.6%) of the title compound, melting point 228°-231° C. $^1$H NMR (DMSO-d$_6$): δ 9.20 (s, 1H), 7.46-7.28 (m, 5H), 7.19 (apparent t, 3H), 7.06 (d, 2H, J=7.4 Hz), 6.92 (d, 2H, J=8.5 Hz), 6.06 (d, 1H, J=8.7 Hz), 5.86 (s, 1H), 5.06 (s, 2H), 4.61 (q, 1H, J=7.8 Hz), 2.96 (dd, 1H, J=13.6, 7.0 Hz), 2.78 (dd, 1H, J=13.6, 7.7 Hz), 1.24 (s, 9H), and 1.03 (apparent t, 12H). IR: principle absorptions at 3300, 2950, 1650, 1550, 1250, 750, and 695 cm$^{-1}$.

EXAMPLE 24

(S)-N-[2,6-bis(1-Methylethyl)phenyl]-α-[(3,3-dimethyl-1-oxobutyl)amino]-4-(phenylmethoxy)benzenepropanamide To a cooled (0° C.) solution of (S)-α-amino-N-[2,6-bis(1-Methylethyl)phenyl]-4-(phenylmethoxy)benzenepropanamide (1.15 g, 2.67 mmol) and triethylamine (0.37 mL, 2.67 mmol) in THF (50 mL) was added tert-butylacetylchloride (0.39 mL, 2.80 mmol) dropwise. The resulting slurry was warmed to 25° C. and stirred (1 hour, 25° C.). The resulting slurry was diluted with ethyl acetate (200 mL). The organic layer was washed with 1.0N aqueous HCl (1×65 mL), with brine (1×65 mL), with saturated aqueous sodium bicarbonate (1×65 mL), with brine again (1×65 mL), then dried (MgSO$_4$) and concentrated. The resulting oil was triturated with ether, and cooled. The resulting solid was collected by filtration, washed with cold ether, and dried in a vacuum oven at 40° C. to yield 1.2 g (85.1%) of the title compound as a white solid, melting point 209°–211.5° C.

Anal. for $C_{34}H_{44}N_2O_3$ Calcd: C, 77.24; H, 8.39; N, 5.30. Found: C, 77.01; H, 8.37; N, 5.00.

$^1$H NMR (CDCl$_3$): δ 7.75 (s, 1H), 7.36 (m, 5H), 7.21 (apparent t, 3H), 7.08 (d, 2H, J=7.4 Hz), 6.89 (d, 2H, J=8.6 Hz), 6.56 (d, 1H, J=8.3 Hz), 5.10 (q, 1H, J=7.9 Hz), 4.99 (s, 2H), 3.13 (m, 2H), 2.71 (m, 2H), 1.99 (s, 2H), 1.07 (d, 6H, J=6.8 Hz), 1.01 (d, 6H, J=6.7 Hz), and 0.88 (s, 9H). IR: principle absorptions at 3300, 2950, 1640, 1500, and 1240 cm$^{-1}$.

EXAMPLE 25

(S)-1,1-Dimethylethyl[2-oxo-1-[[4-(phenylmethoxy)phenyl]methyl]-2-[(2,4,6-trifluorophenyl)amino]ethyl]carbamate Employing the method of Example 20, but using 2,4,6-trifluoroaniline instead of 2,6-diisopropylaniline, the title compound was prepared, melting point 145°–155° C. dec. $^1$H NMR (CDCl$_3$): δ 7.92 (br s, 1H), 7.36 (m, 5H), 7.16 (d, 2H, J=8.5 Hz), 6.91 (d, 2H, J=8.5 Hz), 6.68 (t, 2H, J=8.1 Hz), 5.23 (br d, 1H, J=7.4 Hz), 5.01 (s, 2H), 4.61 (br s, 1H), 3.09 (dd, 2H, J=6.45, 6.45), and 1.39 (s, 9H). IR: principle absorptions at 3300, 1680, 1530, 1250, 1170, 1120, and 1050.

EXAMPLE 26

(S)-α-Amino-4-(phenylmethoxy)-N-(2,4,6-trifluorophenyl)benzenepropanamide

Employing the method of Example 22, but using (S)-1,1-dimethylethyl[2-oxo-1-[[4-(phenylmethoxy)phenyl]methyl]-2-[(2,4,6-trifluorophenyl)amino]ethyl]carbamate instead of (S)-1,1-dimethylethyl[[2,6-bis(1-Methylethyl)phenyl]amino]-2-oxo-1-[[4-(phenylmethoxy)phenyl]methyl]ethyl]carbamate, the title compound was prepared, mp 80.5°–86.5° C.

Anal for $C_{22}H_{19}F_3N_2O_2$: Calcd: C, 66.00; H, 4.78; N, 7.00. Found: C, 65.89; H, 4.68; N, 6.61.

$^1$H NMR (CDCl$_3$): δ 8.88 (s, 1H), 7.38 (m, 5H), 7.17 (d, 2H, J=8.6 Hz), 6.73 (t, 2H, J=8.1 Hz), 5.04 (s, 2H), 3.78 (dd, 1H, J=8.8, 4.2 Hz), 3.25 (dd, 1H, J=14.0, 4.2 Hz), 2.85 (dd, 1H, J=14.0, 8.8 Hz), and 1.74 (br s, 2H). IR: principle absorptions at 3300, 1670, 1600, 1550, 1520, 1450, 1250, 1130, and 1050.

EXAMPLE 27

(S)-α-[[[(1,1-Dimethylethyl)amino]carbonyl]amino]-4-(phenylmethoxy)-N-(2,4,6-trifluoro-phenyl)benzenepropanamide Employing the method of Example 23, but using (S)-α-amino-4-(phenylmethoxy)-N-(2,4,6-trifluorophenyl)benzenepropanamide instead of (S)-α-amino-N-[2,6-bis(1-Methylethyl)phenyl]-4-(phenylmethoxy)-benzenepropanamide, the title compound was prepared, mp 195°–196° C. dec.

Analyzed for $C_{27}H_{28}F_3N_3O_3$: Calcd: C, 64.92; H, 5.65; N, 8.41. Found: C, 64.74; H, 5.60; N, 8.21.

$^1$H NMR (CDCl$_3$): δ 8.91 (s, 1H), 7.04 (m, 5H), 6.85 (d, 2H, J=8.6 Hz), 6.55 (d, 2H, J=8.6 Hz), 6.40 (apparent t, 2H), 5.67 (d, 1H, J=8.3), 5.44 (s, 1H), 4.69 (s, 2H), 4.40 (apparent q, 1H), 2.78 (dd, 1H, J=13.9, 6.1 Hz), 2.63 (dd, 1H, J=13.9, 6.9 Hz), and 0.93 (s, 9H). IR: principle absorptions at 3400, 3200, 3050, 2950, 1640, 1540, 1450, 1250, 1140, and 1050 cm$^{-1}$.

EXAMPLE 28

(S)-α-[(3,3-Dimethyl-1-oxobutyl)amino]-4-(phenylmethoxy)-N-(2,4,6-trifluorophenyl)benzenepropanamide Employing the method of Example 24, but using (S)-α-amino-4-(phenylmethoxy)-N-(2,4,6-trifluorophenyl)benzenepropanamide instead of (S)-α-amino-N-[2,6-bis(1-Methylethyl)phenyl]-4-(phenylmethoxy)benzenepropanamide, the title compound was prepared, mp 150°–157° C.

Analyzed for $C_{28}H_{29}F_3N_2O_3$: Calcd: C, 67.46; H, 5.86; N, 5.62. Found: C, 67.58; H, 5.87; N, 5.38.

$^1$H NMR (CDCl$_3$): δ 8.58 (s, 1H), 7.36 (m, 5), 7.16 (d, 2H, J=8.5 Hz), 6.87 (d, 2H, J=8.5 Hz), 6.64 (apparent t, 2H), 6.52 (d, 1H, J=8.1 Hz), 5.09 (apparent q, 1H), 4.99 (s, 2H), 3.17 (dd, 1H, J=14.1, 6.5 Hz), 3.04 (dd, 1H, J=14.1, 7.7 Hz), 2.01 (s, 2H), and 0.89 (s, 9H). IR: principle absorptions at 3300, 1650, 1550, 1520, 1450, 1240, 1120, 1000.

EXAMPLE 29

(S)-1,1-Dimethylethyl[2-[[2,6-bis(1-methylethyl)phenyl]amino]-1-(1H-indol-3-ylmethyl)-2-oxoethyl]carbamate Employing the method of Example 20, but using N-boc-(L)-pryptophan, instead of N-boc-O-benzyl-(L)-tyrosine, the title compound was prepared, mp 87°–99° C. dec.

Analyzed for $C_{28}H_{37}N_3O_3$: Calcd: C, 72.54; H, 8.04; N, 9.06. Found: C, 72.18; H, 7.70; N, 8.59.

$^1$H NMR (CDCl$_3$): δ 8.19 (s, 1H), 8.73 (d, 1H, J=7.4 Hz), 7.38–7.02 (m, 8H), 5.20 (br d, 1H), 4.74 (apparent q, 1H, J=6.5 Hz), 3.34 (d, 2H, J=6.5 Hz), 2.70 (br s, 2H), 1.47 (s, 9H), 1.05 (d, 6H, J=6.8 Hz), and 1.00 (br d, 6H, J=7.4 Hz). IR: principle absorptions at 3400, 2950, 1680, 1500, 1170, and 750 cm$^{-1}$.

EXAMPLE 30

(S)-α-Amino-N-[2,6-bis(1-methylethyl)-phenyl]-1H-indole-3-propanamide

Employing the method of Example 22, but using (S)-1,1-dimethyl[2-[[2,6-bis(1-Methylethyl)phenyl]amino]-1-(1H-indol-3-ylmethyl)-2-oxoethyl]carbamate instead of (S)-1,1-dimethylethyl[2-[[2,6-bis(1-Methylethyl)phenyl]amino]-2-oxo-1-[[4-(phenylmethoxy)- phenyl]methyl]ethyl]carbamate, the title compound was prepared, mp 185°–187° C.

Analyzed for $C_{23}H_{29}N_3O$: Calcd: C, 76.00; H, 8.04; N, 11.56.

Found: C, 75.78; H, 8.08; N, 11.25.

$^1$H NMR (CDCl$_3$): δ 9.77 (s, 1H), 8.96 (s, 1H), 7.70 (d, 1H, J=7.7 Hz), 7.41–7.05 (m, 7H), 3.93 (dd, 1H, J=9.4, 3.9 Hz), 3.49 (m, 1H), 3.00 (m, 3H), 1.66 (br s, 2H), and 1.67 (overlapping d, d, 12H). IR: principle absorptions at 3300, 2950, 1670, and 750 cm$^{-1}$. 15 Example 31

EXAMPLE 31

(S)-(1,1-Dimethylethyl[1-(1H-indol-3-ylmethyl)-2-oxo-2-[2,4,6-trifluorophenyl)amino]ethyl]carbamate Employing the method of Example 20, but using 2,4,6-trifluoroaniline instead of 2,6-diisopropylaniline and N-boc-(L)-tryptophan instead of N-boc-O-benzyl-(L)-tyrosine, the title compound was prepared, mp 69°–85° C. dec.

Analyzed for $C_{22}H_{22}F_3N_2O_3$: Calcd: C, 60.97; H, 5.12. Found: C, 61.37; H, 5.28.

$^1$H NMR (CDCl$_3$): δ 8.16 (s, 1H), 7.70 (d, 1H, J=7.6 Hz), 7.46–7.11 (m, 5H), 6.69 (apparent t, 2H), 5.17 (br s, 1H), 4.68 (br s, 1H), 3.33 (apparent br t, 2H), and 1.43 (s, 9H). IR: principle absorptions at 3400, 1700, 1530, 1450, 1350, 1180, 1140, 1050, and 750 cm$^{-1}$.

EXAMPLE 32

(S)-α-Amino-N-(2,4,6-trifluorophenyl)-1H-indole-3-propanamide

Employing the method of Example 22, but using (S)-(1,1-dimethylethyl[1-1H-indol-3-ylmethyl)-2-oxo-2-[2,4,6-trifluorophenyl)amino]ethyl]carbamate instead of (S)-1,1-dimethylethyl[2-[[2,6-bis(1-Methylethyl)phenyl]amino]-2-oxo-1-[[4-(phenylmethoxy)phenyl]methyl]ethyl]carbamate, the title compound was prepared, mp 45°–55° C.

EXAMPLE 33

(S)-[2-[[2,6-bis(1-Methylethyl)phenyl]-amino]-2-oxo-1-phenylethyl]carbamic acid, phenylmethyl ester Employing the method of Example 20, but using N-CBZ-(L)-phenylglycine instead of N-boc-O-benzyl-(L)-tyrosine, the title compound was prepared, mp 199°–202.5° C.

EXAMPLE 34

2-[(Diphenylmethyl)amino]-N-(2,4,6-trimethoxyphenyl)acetamide

The title compound was prepared according to the procedure for Example 4 by substituting 2,4,6-trimethoxy aniline for 2,6-diisopropylaniline. 3.93 g (48%). NMR (CDCl$_3$) δ 3.42 (2H, s), δ 3.78 (9H, s), δ 4.98 (1H, s), δ 6.16 (2H, s), δ 3.78 (9H, s), δ 4.98 (1H, s), δ 6.16 (2H, s), δ 7.05–7.25 (10H, m), δ 8.20 (1H, s). IR (LF) 3004, 1671, 1598, 1519, 1205, 1130, 703 cm$^{-1}$.

EXAMPLE 35

(S)-[1-[[[2,6-bis(1-Methylethyl)-phenyl]amino]carbonyl]-3-(methylthio)propyl]carbamic acid, 1,1-dimethylethyl ester Employing the method of Example 20, but using N-boc-(L)-methionine instead of N-boc-O-benzyl-(L)-tyrosine, the title compound was prepared, mp 187°–189° C.

EXAMPLE 36

(S)-[2-[[2,6-bis(1-Methylethyl)phenyl]-amino]-1-methylethyl]carbamic acid, 1,1-dimethylethyl ester Employing the method of Example 20, but using N-boc-(L)-alanine instead of N-boc-O-benzyl-(L)-tyrosine, the title compound was prepared, mp 179°–182° C.

EXAMPLE 37

(S)-[2-[[2,6-bis(1-Methylethyl)phenyl]-amino]-2-oxo-1-(phenylmethyl)ethyl]carbamic acid, 9H-fluoren-9-ylmethyl ester Employing the method of Example 20, but using N-FMOC-(L)-phenylalanine instead of N-boc-O-benzyl-(L)-tyrosine, the title compound was prepared, mp 210°–212.5° C.

EXAMPLE 38

(S)-[2-[[2,6-bis(1-Methylethyl)phenyl]-amino]-2-oxo-1-[[4-(phenylmethoxy)phenyl]methyl]-ethyl]carbamic acid, 9H-fluoren-9-ylmethyl ester Employing the method of Example 20, but using N-FMOC-O-benzyl-(L)-tyrosine instead of N-boc-O-benzyl-(L)-tyrosine, the title compound was prepared, mp 168.5°–171° C.

EXAMPLE 39

(±)-N-[2,6-bis(1-Methylethyl)phenyl]-α-[(phenylmethyl)amino]benzeneacetamide

Step 1—Preparation of (±)-N-[2,6-bis(1-methylethyl)phenyl]-α-bromobenzeneacetamide A solution of α-bromophenylacetic acid (19.3 g, 89.7 mmol) in thionylchloride (100 mL) was refluxed (2 hours), cooled (25° C.), and stirred (25° C., 14 hours). The resulting solution was concentrated in vacuo, diluted with ether, and concentrated again to yield 21.0 g (100%) of α-bromophenylacetylchloride as a slightly yellow oil which was used without further purification.

The α-bromophenylacetylchloride (21.0 g, 89.7 mmol) was added slowly via pipet to a cooled (0° C.) solution of 2,6-diisopropylaniline (15.9 g, 89.7 mmol) and triethylamine (12.5 mL, 89.7 mmol) in ethyl acetate (1600 mL). The resulting slurry was warmed (25° C.) then stirred (1 hour). The resulting mixture was diluted with ethyl acetate (1000 mL) and dichloro methane (500 mL), then washed with water (1000 mL), with 0.5N aqueous HCl (2×1000 mL), with saturated aqueous sodium bicarbonate (1×600 mL), with brine (1×600 mL), then dried (MgSO$_4$) and concentrated to a solid. The solid was recrystallized from ethyl acetate to yield 27.2 g (81.0%) of (±)-N-[2,6-bis(1-Methylethyl)-phenyl]-α-bromobenzeneacetamide as a white solid, mp 207°–209.5° C.

Step 2—Preparation of (±)-N-[2,6-bis(1-methylethyl)phenyl]-α-[phenylmethyl)amino]benzeneacetamide A solution of (±)-N-[2,6-bis(1-Methylethyl)phenyl]-α-bromobenzeneacetamide (4.3 g, 12 mmol), benzylamine (1.8 g, 18 mmol), and triethylamine (8.0 mL, 57 mmol) in toluene was refluxed (96 hours) then cooled and concentrated in vacuo. The residue was taken up in ethyl acetate (300 mL), washed with water (2×100 mL), with saturated aqueous sodium bicarbonate (1×100 mL), with brine (1×100 mL), then dried (MgSO$_4$) and concentrated to a solid. The solid was recrystallized from ethyl acetate/hexane to yield 3.35 g (72.8%) of the title compound as a white solid, mp 134°–137° C.

EXAMPLE 40

(±)-N-[2,6-bis(1-Methylethyl)phenyl]-2-[(2,2-diphenylethyl)amino]propanamide

Step 1—Preparation of (±)-N-[2,6-bis(1-methylethyl)phenyl-2-bromopropanamide

Bromopropionylbromide (9.4 mL, 90 mmol) was added dropwise to a cooled (0° C.) solution of 2,6-diisopropylaniline (15.9 g, 89.7 mmol), and triethylamine (12.5 mL, 89.7 mmol) in ethyl acetate (1600 mL). The resulting slurry was warmed (25° C.) and stirred (1.5 hours, 25° C.). The resulting mixture was diluted with ethyl acetate (500 mL), washed with water (1×1000 mL), with 0.5N aqueous HCl (2×600 mL), with saturated aqueous sodium bicarbonate (1×600 mL), with brine (1×600 mL), then dried (MgSO$_4$) and concentrated. The resulting solid was washed with cold ether and dried in a vacuum oven at 40° C. (16 hours) to yield 21.33 g (76.1%) of (±)-N-[2,6-bis(1-Methylethyl)phenyl]-2-bromopropanamide as a white solid.

Anal. for C$_{15}$H$_{22}$BrNO: Calcd: C, 57.70; H, 7.10; N, 4.49. Found: C, 57.81; H, 7.01; N, 4.37.

Step 2—Preparation of (±)-N-[2,6-bis(1-methylethyl)phenyl]-2-[(2,2-diphenylethyl)amino]propanamide A solution of (±)-N-[2,6-bis(1-Methylethyl)-phenyl]-2-bromopropanamide (2.0 g, 6.4 mmol), 2,2-diphenylethylamine (1.26 g, 6.41 mmol) and triethylamine (1.8 mL, 13 mmol) in acetonitrile (30 mL) was refluxed (96 hours), then cooled (25° C.). The resulting slurry was diluted with ethyl acetate (300 mL), washed with water (1×100 mL), with saturated aqueous sodium bicarbonate (1×100 mL), with brine (1×100 mL), then dried (MgSO$_4$) and concentrated. Crystallization from ethyl acetate/hexane yielded 2.0 g (72.8%) of the title compound as a white solid, mp 206.5°–208.5° C.

EXAMPLE 41

(S)-α-N-(2,6-Diisopropylphenyl)benzenepropanamide

Ten g N-L-phenylalanine and 4.55 mL (0.0415 mol) N-methyl morpholine were dissolved in 200 mL dichloromethane. The solution was cooled to −10° C. and 5.42 mL (0.0415 mol) iso-butyl chloroformate was added dropwise. After 30 minutes 8.5 mL (0.045 mole) of 2,6-diisopropylaniline was added. The cool bath was removed and the reaction was stirred for 64 hours at room temperature. The reaction mixture was diluted with 100 mL dichloromethane and was washed in separation funnel with 1N citric acid and 0.5N aqueous sodium hydroxide. The organic layer was dried over magnesium sulfate, filtered, and evaporated. The residue was crystallized from dichloromethane/petrol ether. Yield: 10.48 g white crystals with mp 192°–193° C.

EXAMPLE 42

(S)-α-(Acetylamino)-N-(2,6-diethylphenyl)benzenepropanamide

Following the procedure of Example 41 only using appropriate amounts of 2,6-diethylaniline and N-acetyl-L-phenylaniline the title compound was obtained, mp 205°–206° C.

EXAMPLE 43

Phenylmethyl(±)-2-[(2,6-dimethylphenyl)amino]-2-oxo-1-(phenylmethyl)ethyl]carbamate Following the procedure of Example 41 only using 2,6-dimethylaniline and N-benzyloxycarbonyl-D,L-phenylaniline the title compound was obtained, mp 164°–165° C.

EXAMPLE 44

Phenylmethyl(±)-2-(2,6-diethylphenyl)amino]-2-oxo-1-(phenylmethyl)ethyl]carbamate Following the procedure of Example 41 only using 2,6-diethylaniline and N-benzyloxycarbonyl-D,L-phenylaniline the title compound was obtained, mp 165°–166° C.

EXAMPLE 45

Phenylmethyl(±)-[2-[[2,6-bis(1-methylethyl)phenyl]amino]-2-oxo-1-(phenylmethyl)ethyl]carbamate Following the procedure of Example 1 only using 2,6-diisopropylaniline and N-benzyloxycarbonyl-D,L-phenylaniline the title compound was obtained, mp 170°–171° C.

EXAMPLE 46

(S)-α-(Acetylamino)-N-[2,6-bis(1-methylethyl)phenyl]-benzenepropanamide

Following the procedure of Example 41 only using 2,6-diisopropylaniline and N-acetyl-L-phenylaniline the title compound was obtained, mp 228°–229° C.

EXAMPLE 47

1,1-Dimethylethyl(S)-2-oxo-1-(phenylmethyl)-2-[(2,4,6-trifluorophenyl)amino]ethyl]carbamate Following the procedure of Example 41 only using 2,4,6-trifluoroaniline and N-t-butoxycarbonyl-L-phenylaniline the title compound was obtained, mp 125°–126° C.

EXAMPLE 48

(S)-α-(Acetylamino)-N-[2,6-dimethylphenyl]benzenepropanamide

Following the procedure of Example 41 only using 2,6-dimethylaniline and N-acetyl-L-phenylaniline the title compound was obtained, mp 217°–218° C.

EXAMPLE 49

(S)-α-Amino-N-[2,6-bis(1-Methylethyl)phenylbenzenepropanamide 9.23 g of 2,6-diisopropylaniline)-N-BOC-L-phenylalanine was suspended in 150 mL 1N hydrochloric acid and was heated to reflux. When the starting material had been dissolved completely, after about 25 minutes the reaction was cooled to room temperature. The reaction mixture was adjusted to pH 12 with sodium carbonate and then it was extracted with dichloromethane extensively. The combined organic extracts were dried over magnesium sulfate, filtered, and concentrated in vacuo. Yield: 6.94 g colorless oil which crystallized upon standing, mp 153°–154° C.,

EXAMPLE 50

(S)-α-Amino-N-(2,4,6-trifluorophenyl)benzenepropanamide

Following the procedure of Example 49 only starting with the product of Example 47, the title compound was obtained. $^1$HNMR (DMSO): δ 7.25 (m, 7H), 3.65 (dd, 1H), 3.32 (s, 2H), 3.05 (dd, 1H), 2.75 (dd, 1H).

EXAMPLE 51

(±)-α-Amino-N-[2,6-bis(1-methylethyl)]benzenepropanamide

Following the procedure of Example 49 only starting with the product of Example 45, the title compound was obtained, mp 153°-154° C.

EXAMPLE 52

(S)-N-[2,6-bis(1-Methylethyl)phenyl]-α-[[(4-methylphenyl)sulfonyl]amino]benzenepropanamide To a solution of 0.61 g (1.88 mmol) (2,6-diisopropylaniline)-L-phenylalanine and 0.3 mL triethylamine in 20 mL dichloromethane at 0° C. was added 0.38 g (2.0 mmol) tosyl chloride. After 30 minutes the cool bath was removed and the reaction was stirred for 16 hours. The reaction mixture was taken up in dichloromethane and washed successively with dilute aqueous citric acid and water. The organic layer was dried over magnesium sulfate, filtered, and evaporated. Obtained was a white powder that was recrystallized from diethyl ether. Yield: 0.75 g, mp 183°-184° C.

EXAMPLE 53

(S)-N-[2,6-bis(1-Methylethyl)phenyl]-α-[(4-chloro-1-oxobutyl)amino]benzenepropanamide Following the procedure of Example 52 only substituting 4-chlorobutrylchloride for tosyl chloride, the title compound was obtained, mp 212°-215° C.

EXAMPLE 54

(±)-α-(Benzyoylamino)-N-[2,6-bis(1-methylethyl)phenyl]benzenepropanamide

Following the procedure of Example 52 only using the product of Example 51 and benzoylchloride, the title compound was obtained, mp 257°-258° C.

EXAMPLE 55

(±)-N-[2,6-bis(1-Methylethyl)phenyl]-α-[(1-oxopentyl)amino]benzenepropanamide

Following the procedure of Example 52 only using the product of Example 51 and valeric anhydride, the title compound was obtained, mp 237°-238° C.

EXAMPLE 56

(S)-α-[[(4-Methylphenyl)sulfonyl]amino]-N-(2,4,6-trifluorophenyl)benzenepropanamide Following the procedure of Example 52 only using the product of Example 50 and tosyl chloride, the title compound was obtained, mp 180°-181° C.

EXAMPLE 57

(±)-cis-N-[2,6-bis(1-Methylethyl)phenyl]-α-(1-oxo-9-octadecenyl)benzenepropanamide Following the procedure of Example 52 only using the product of Example 51 and 9-octadecenoyl chloride, the title compound was obtained. $^1$HNMR (CDCl$_3$) δ 7.45-7.05 (m, 9Y), 6.23 (d, 1H), 5.37 (m, 2H), 4.92 (q, 1H), 3.24 (dd, 1H), 3.14 (dd, 1H), 3.73 (broad s, 2H), 2.20 (t, 2H), 2.05 (m, 4H), 1.7-1.5 (m, 4H), 1.30 (m, 18H), 1.08 (d, 12H), 0.88 (t, 3H).

EXAMPLE 58

N-[2,6-bis(1-Methylethyl)phenyl]-α-[[(phenylamino)ethyl]amino]carbonyl]amino]benzenepropanamide 0.65 g (2.0 mol) (2.6-diisopropylaniline)-L-phenylalanine was dissolved in 2 mL dichloromethane. Upon addition of 0.25 mL (2.4 mol) phenylisocyanate a white precipitate began to form. After four hours the precipitate was collected, washed with diethyl ether and dried in vacuum oven at 50° C. Yield: 0.62 g white solid, mp 270°-271° C.

EXAMPLE 59

N-[2,6-bis(1-Methylethyl)phenyl]-α-[[[(1,1-dimethylethyl)amino]carbonyl]amino]benzenepropanamide Following the procedure of Example 58 only using the product of Example 51 and t-butylisocyanate, the title compound was obtained, mp 241°-242° C.

EXAMPLE 60

(S)-N-[2,6-bis(1-Methylethyl)phenyl]-α-[[(butylamino)thioxomethyl]amino]benzenepropanamide Following the procedure of Example 58 only substituting n-butylthioisocyanate for phenylisocyanate, the title compound is obtained, mp 214°-215° C.

EXAMPLE 61

(S)-α-[[(Phenylamino)carbonyl]amino]-N-(2,4,6-trifluorophenyl)benzenepropanamide Following the procedure of Example 58 only using the product of Example 50 and phenylisocyanate, the title compound was obtained, mp 225°-233° C.

EXAMPLE 62

(S)-α-[[[(1,1-Dimethylethyl)amino]carbonyl]amino]-N-(2,4,6-trifluorophenyl)benzenepropanamide Following the procedure of Example 58 only using the product of Example 50 and t-butylisocyanate, the title compound was obtained, mp 205°-206° C.

EXAMPLE 63

(S)-N-[2,6-bis(1-Methylethyl)phenyl]-α-[[[(phenylmethyl)amino]carbonyl]amino]benzenepropanamide Following the procedure of Example 58 only using the product of Example 49 and phenylisocyanate, the title compound was obtained, mp 240°-241° C.

EXAMPLE 64

(S)-α-[[(Butylamino)carbonyl]amino]N-(2,4,6-trifluorophenyl)benzenepropanamide

Following the procedure of Example 58 only using the product of Example 50 and n-butylisocyanate, the title compound was obtained, mp 217°-218° C.

EXAMPLE 65

2-Acetyl(diphenylmethyl)amino]-N-[2,6-bis(1-methylethyl)phenyl]acetamide

Acetic anhydride (40 mL) was added to the product from Example 4 (0.60 g) and the resulting mixture was stripped to dryness on the rotary evaporator at 60° C.

This process was repeated and EtOAc/hexane, 1/1 was added to the residue and a white solid resulted. Hexane was added and the solid was collected by filtration 0.48 g (73%). NMR (CDCl3) δ 1.09 (12H, d), δ 2.32 (3H, s), δ 2.73 (2H, m), δ 4.25 (2H, s), δ 6.35 (1H, s), δ 7.0–7.5 (13H, m), δ 7.81 (1H, s). IR (KBr) 3437, 2964, 1634, 1383, 700 cm$^{-1}$.

EXAMPLE 66

[2-[[2,6-bis(1-Methylethyl)phenyl]amino]-2-oxoethyl]-(diphenylmethyl)carbamic acid methyl ester Several milliliters of methylchloroformate was added to the product from Example 4 (0.60 g) in a mixture of excess NEt3 and EtOAc at room temperature. Vigorous outgassing occurred with the formation of a precipitate. The solution was stripped to dryness and the residue taken up in a mixture of 50 mL THF and 50 mL saturated NaHCO3 solution. Excess methyl chloroformate was added at room temperature. This solution was allowed to sit 5 days at room temperature. The reaction mixture was diluted with EtOAc and washed with aqueous K2CO3 solution and aqueous NaCl solution. The organic layer was dried over MgSO4, filtered, and concentrated to a white solid. The solid was slurried in hexane/EtOAc 9/1 and collected by filtration. 0.55 g (80%). NMR (CDCl3) δ 1.06 (12H, d), δ 2.56 (2H, m), δ 3.84 (3H, s), δ 4.20 (2H, s), δ 6.80 (1H, bs), δ 7.0–7.5 (13H, m). IR (KBr) 3443, 2963, 1705, 1685, 699 cm$^{-1}$.

EXAMPLE 67

N-[[[2-[[2,6-bis(1-Methylethyl)phenyl]amino]-2-oxoethyl](diphenylmethyl)amino]carbonyl]glycine ethyl ester Ethylisocyanato acetate (1 mL) was added to a mixture of the product from Example 4 (0.60 g) and ethyl acetate (100 mL) at room temperature. A white solid resulted upon concentration to dryness. Ethyl acetate was added to the solid and ethylisocyanato acetate (1 mL) was again added. The reaction mixture was concentrated to dryness. A white solid remained and was collected by filtration from a slurry in hexane/EtOAc, 1/1. (0.49 g (62%). NMR (CDCl3) δ 1.09 (12H, d), δ 1.26 (3H, t), δ 2.72 (2H, m), δ 3.99 (2H, d), δ 4.13–4.22 (4H, m), δ 5.70 (1H, bt), δ 6.69 (1H, s), δ 7.0–7.5 (13H, m). IR (KBr) 3389, 2963, 1757, 1652, 1641, 1497, 1194, 700.

EXAMPLE 68

N-[2-[[2,6-bis(1-Methylethyl)phenyl]amino]-2-oxoethyl-N-(diphenylmethyl)benzamide Benzoyl chloride (0.4 mL) was added to a mixture of the product from Example 4, excess NEt3, and EtOAc at room temperature. The reaction mixture was allowed to sit for 8 days at room temperature then diluted with EtOAc, washed with K2CO3 (aq) and NaCl (aq), dried over MgSO4, filtered, and stripped to an oil/solid. The oil/solid was triturated with hexane and the resulting solid was collected by filtration. (0.66 g) (87%). NMR (CDCl3) δ 1.10 (12H, d), δ 2.78 (2H, m), δ 4.39 (2H, bs), δ 6.34 (1H, bs), δ 7.0–7.6 (18, m). IR (KBr) 3437, 1623, 1496, 699 cm$^{-1}$.

EXAMPLE 69

N-[2,6-bis(1-Methylethyl)phenyl]-2-[(diphenylmethyl)[(phenylamino)carbonyl]amino]acetamide Excess phenylisocyanate (0.44 g) was added to a mixture of the product from Example 4 (0.60 g) in 100 mL EtOAc at room temperature. After sitting for a short period of time at room temperature, the solvent was removed in vacuo. EtOAc was added to the residue and allowed to sit 2 days at room temperature. The ethyl acetate was removed on the rotary evaporator. The residual solid was slurried in hexane/EtOAc, 1/1 and collected by filtration. (0.82 g) (100%). NMR (CDCl3) δ 1.06 (12H, d), δ 2.66 (2H, m), δ 4.24 (2H, s), δ 6.44 (1H, bs), δ 6.9–7.5 (18H, m), δ 7.93 (1H, bs). IR (KBr) 3391, 2964, 1648, 1531, 1444, 752, 700 cm$^{-1}$.

EXAMPLE 70

N-[2,6-bis(1-Methylethyl)phenyl]-2-[(2,2-diphenylethyl)amino]acetamide

The title compound was prepared according to the procedure for Example 4 by substituting 2,2-diphenylethylamine for benzhydryl amine. 13.25 g (68%). NMR (CDCl3) δ 1.16 (12H, d), δ 2.95 (2H, m), δ 3.4 (2H, d), δ 3.48 (2H, s), δ 4.18 (1H, t), δ 7.0–7.4 (13H, m), δ 8.59 (1H, s). IR (KBr) 3210, 2963, 1674, 1652, 1641, 1495, 1136, 698 cm$^{-1}$.

EXAMPLE 71

N-[2,6-bis(1-Methylethyl)phenyl]-2-[(phenylmethyl)amino]acetamide

Bromoacetylbromide (4.5 mL) was added portionwise to a mixture of 8.85 g 2,6-diisopropylaniline and 7.0 mL triethylamine in 300 mL EtOAc at 0° C. Upon completing the addition, excess triethylamine and 5.4 g benzylamine were added and the entire mixture was heated on the steambath for 30 minutes. The reaction mixture was allowed to sit overnight at room temperature, and was then filtered, concentrated, and filtered through silica gel (70–230 mesh) using hexane/EtOAc, 1/1, as eluant. A total of 15.62 g (96%) of the title product was obtained.

Anal for $C_{21}H_{28}N_2O$: Calcd: C, 77.74; H, 8.70; N, 8.63. Found: C, 76.88; H, 8.46; N, 8.25.

IR (KBr) 3336, 3289, 2955, 1677, 1499, 750 cm$^{-1}$.

EXAMPLE 72

2-[(Diphenylmethyl)amino]-N-(2,4,6-trimethoxyphenyl)acetamide

When in the procedure of Example 71 an appropriate amount of benzyhydrylamine was substituted for benzylamine and an appropriate amount of 2,4,6-trimethoxyaniline was substituted for 2,6-diisoproplyaniline and the general procedure of Example 71 was followed the title compound was obtained. Total yield, 3.93 g (48%).

Anal for $C_{24}H_{26}N_2O_4$: Calcd: C, 70.92; H, 6.45; N, 6.89. Found: C, 70.53; H, 6.61; N, 6.52.

IR (film) 3004, 2940, 1684, 1676, 1598, 1519, 1130, 750 cm$^{-1}$.

EXAMPLE 73

N-[2,6-bis(1-Methylethyl)phenyl]-2-[[[4-(dimethylamino)phenyl]methyl]amino]acetamide When in the procedure of Example 71 an appropriate amount of 4-dimethylaminobenzylamine was substituted for benzylamine and the general procedure of Example 71 was followed the title compound was obtained. Total yield, 1.29 g (16%).

Anal for $C_{23}H_{33}N_3O$: Calcd: C, 75.16; H, 9.05; N, 11.43. Found: C, 74.61; H, 9.10; N, 10.98.

IR (film) 3284, 3263, 3245, 2932, 1725, 1684, 1675, 1653, 1506, 910, 730 cm$^{-1}$.

EXAMPLE 74

N-(2,6-Difluorophenyl)-2-[(diphenylmethyl)amino]acetamide

When in the procedure of Example 71 an appropriate amount of benzhydrylamine was substituted for benzylamine and an appropriate amount of 2,6-difluoroaniline was substituted for 2,6-diisoproplyaniline and the general procedure of Example 71 was followed the title compound was obtained. Total yield, 4.53 g (26%).

Anal for $C_{21}H_{18}F_2N_2O$: Calcd: C, 71.58; H, 5.15; N, 7.95. Found: C, 71.96; H, 5.49; N, 7.22.

IR (film) 3027, 1694, 1685, 1521, 1516, 1016, 783, 743 cm$^{-1}$.

EXAMPLE 75

N-(2,6-Diethylphenyl)-2-[(diphenylmethyl)amino]acetamide

When in the procedure of Example 71 an appropriate amount of benzhydrylamine was substituted for benzylamine and an appropriate amount of 2,6-diethylaniline was substituted for 2,6-diisoproplyaniline and the general procedure of Example 71 was followed the title compound was obtained. Total yield, 6.67 g (36%).

Anal for $C_{25}H_{28}N_2O$: Calcd: C, 80.61; H, 7.58; N, 7.52. Found: C, 80.36; H, 7.58; N, 7.36.

IR (KBr) 3238, 3231, 2966, 1652, 1531, 1454, 748, 683 cm$^{-1}$.

EXAMPLE 76

N-(2,6-Dimethylphenyl)-2-[(diphenylmethyl)amino]acetamide

When in the procedure of Example 71 an appropriate amount of benzhydrylamine was substituted for benzylamine and an appropriate amount of 2,6-dimethylaniline was substituted for 2,6-diisoproplyaniline and the general procedure of Example 71 was followed the title compound was obtained. Total yield, 7.08 g (41%).

Anal for $C_{23}H_{24}N_2O$: Calcd: C, 80.20; H, 7.02; N, 8.13. Found: C, 79.79; H, 7.08; N, 8.04.

IR (KBr) 3233, 3032, 1657, 1538, 1469, 1297, 1271, 960, 702 cm$^{-1}$.

EXAMPLE 77

N-[2,6-bis(1-Methylethyl)phenyl]-2-(9H-fluoren-9-ylamino)acetamide

When in the procedure of Example 71 an appropriate amount of 9-fluorenylamine was substituted for benzylamine and the general procedure of Example 71 was followed the title compound was obtained. Total yield, 7.19 g (36%).

Anal for $C_{27}H_{30}N_2O$: Calcd: C, 81.37; H, 7.59; N, 7.04. Found: C, 81.05; H, 7.68; N, 6,84.

IR (KBr) 3309, 1655, 1499, 1449, 740 cm$^{-1}$.

EXAMPLE 78

4-[[2-[[2,6-bis(1-Methylethyl)phenyl]amino]-2-oxoethyl](phenylmethyl)amino]-4-oxo-butanoic acid A mixture of 0.65 g of the product from Example 71 and 0.22 g succinic anhydride in 10 mL EtOAc was heated on the steambath until solution occurred. The reaction mixture was concentrated to dryness, redissolved in EtOAc, heated on the steambath for 30 minutes, allowed to sit overnight at room temperature, concentrated to dryness, and triturated with hexane/EtoAc, 20/1 to give the product as a solid. Total yield, 0.66 g (78%).

Anal for $C_{25}H_{32}N_2O_4$. Calcd: C, 70.73; H, 7.60; N, 6.60. Found: C, 70.40; H, 7.59; N, 6.36.

IR (KBr) 3259, 3233, 3216, 1683, 1669, 1653, 1532, 1456, 1401, 700 cm$^{-1}$.

EXAMPLE 79

2-[Acetyl(1,1-dimethyl-2-phenylethyl)amino]-N-[2,6-bis(1-methylethyl)phenyl]acetamide The produce of Example 5 (0.73 g) and 30 mL acetic anhydride was heated on the steambath for 2 hours. The excess acetic anhydride was removed on the rotary evaporator and the residue triturated with hexane/EtoAc, 40/1.

The resulting solid was collected by filtration to give the title product 0.59 g (73%).

Anal for $C_{26}H_{36}N_2O_2$: Calcd: C, 76.43; H, 8.88; N, 6.86. Found: C, 76.22; H, 8.77; N, 6.75.

IR (KBr) 3476, 3433, 3272, 1698, 1645, 1637, 1213, 702 cm$^{-1}$.

EXAMPLE 80

N-[[[2-[[2,6-bis(1-Methylethyl)phenyl]amino]-2-oxoethyl](2,2-diphenylethyl)amino]carbonyl]glycine, ethyl ester A mixture of 0.76 g of the product of Example 70 and 0.31 g ethyl isocyanato acetate in 10 mL EtOAc was heated on the steambath for 1 hour. The reaction mixture was concentrated to dryness and the residue triturated with hexane/EtoAc 10/1 to give a solid which was collected by filtration to give the title compound. Total yield, 0.64 g (64%).

Anal for $C_{33}H_{39}N_3O_4$: Calcd: C, 73.17; H, 7.26; N, 7.76. Found: C, 72.75; H, 7.65; N, 7.56.

IR (KBr) 3356, 2962, 1750, 1747, 1744, 1663, 1653, 1522, 1490, 702 cm$^{-1}$.

EXAMPLE 81

2-[Acetyl[[4-(dimethylamino)phenyl]methyl]amino]-N-[2,6-bis(1-methylethyl)phenyl]acetamide When in the procedure of Example 79 an appropriate amount of the product from Example 73 was substituted for the product of Example 5 the title compound was obtained. Total yield, 0.41 g (73%).

Anal for $C_{25}H_{33}N_3O_2$: Calcd: C, 73.31; H, 8.61; N, 10.26. Found: C, 72.97; H, 8.76; N, 10.11.

IR (KBr) 3292, 3244, 2961, 1695, 1683, 1662, 1652, 1646, 1524, 1444, 1235, 805 cm$^{-1}$.

EXAMPLE 82

N-[2-[[2,6-bis(1-Methylethyl)phenyl]amino]-2-oxoethyl]-N-(phenylmethyl)acetamide When in the procedure of Example 79 an appropriate amount of the product of Example 71 was substituted for the product of Example 5 the title compound was obtained. Total yield, 0.51 g (79%).

Anal for $C_{23}H_{30}N_2O_2$: Calcd: C, 75.38; H, 8.25; N, 7.64. Found: C, 75.01; H, 8.30; N, 7.35.

IR (KBr) 2964, 1666, 1645, 1431, 736 cm$^{-1}$.

EXAMPLE 83

N-(2,6-Dimethylphenyl)-2-[[N-(diphenylmethyl)-N-(phenylamino)carbonyl]amino]acetamide When in the procedure of Example 80 an appropriate amount of the product of Example 76 was substituted for the product of Example 70, and an appropriate amount of phenylisocyanate was substituted for ethyl isocyanato acetate and the general procedure of Example 80 was followed the title compound was obtained. Total yield, 1.30 g (96%).

Anal for $C_{30}H_{29}N_3O_2.\frac{1}{3} C_4H_8O_2$: Calcd: C, 76.35; H, 6.47; N, 8.52. Found: C, 75.18; H, 6.40; N, 7.90.

IR (KBr) 3242, 2961, 1659, 1522, 1056, 697 cm$^{-1}$.

EXAMPLE 84

N-[2,6-bis(1-Methylethyl)phenyl]-2-[(diphenylmethyl)[[(2-methoxyphenyl)amino]carbonyl]amino]acetamide When in the procedure of Example 80 an appropriate amount of 2-methoxyphenylisocyanate was substituted for ethyl isocyanato acetate and an appropriate amount of the product of Example 4 was substituted for the product of Example 70 and the general procedure of Example 80 was followed the title compound was obtained. Total yield, 1.56 g (76%).

Anal for $C_{35}H_{39}N_3O_3$: Calcd: C, 76.47; H, 7.15; N, 7.64. Found: C, 76.51; H, 7.09; N, 7.27.

IR (KBr) 2963, 1695, 1683, 1662, 1652, 1496, 748 cm$^{-1}$.

EXAMPLE 85

N-[[[2-[[2,6-bis(1-Methylethyl)phenyl]amino]-2-oxoethyl](phenylmethyl)amino]carbonyl]glycine, ethyl ester When in the procedure of Example 80 an appropriate amount of the product of Example 71 was substituted for the product of Example 70 and the general procedure of Example 80 was followed the title compound was obtained. Total yield, 0.77 g (88%).

Anal for $C_{26}H_{35}N_3O_4$: Calcd: C, 68.85; H, 7.78; N, 9.26. Found: C, 69.30; H, 7.79; N, 9.05.

IR (KBr) 3362, 3238, 2962, 1732, 1649, 1515, 1262, 701 cm$^{-1}$.

EXAMPLE 86

N-[2,6-bis(1-Methylethyl)phenyl]-2-[[(phenylamino)carbonyl](phenylmethyl)amino]acetamide When in the procedure of Example 80 an appropriate amount of phenylisocyanate was substituted for ethyl isocyanato acetate and an appropriate amount of the product of Example 71 was substituted for the product of Example 70 and the general procedure of Example 80 was followed the title compound was obtained. Total yield, 0.73 g (81%).

Anal for $C_{28}H_{33}N_3O_2$: Calcd: C, 75.82; H, 7.50; N, 9.47. Found: C, 75.90; H, 7.55; N, 9.33.

IR (KBr) 3261, 2962, 1683, 1667, 1652, 1533, 1445, 1311 cm$^{-1}$.

EXAMPLE 87

N-[2,6-bis(1-Methylethyl)phenyl]-2-[9H-fluoren-9-yl[(propylamino)carbonyl]amino]acetamide When in the procedure of Example 80 an appropriate amount of the product of Example 77 was substituted for the product of Example 70 and an appropriate amount of propylisocyanate was substituted for ethyl isocyanato acetate and the general procedure of Example 80 was followed the title compound was obtained. Total yield, 0.73 g (68%).

Anal for $C_{31}H_{37}N_3O_2$: Calcd: C, 76.98; H, 7.71; N, 8.69. Found: C, 76.63; H, 7.79; N, 8.47.

IR (KBr) 3278, 2966, 1736, 1719, 1636, 1539, 1452, 1230, 997, 701 cm$^{-1}$.

EXAMPLE 88

N-[2,6-bis(1-Methylethyl)phenyl]-2-[9H-fluoren-9-yl[(phenylamino)carbonyl]amino]acetamide When in the procedure of Example 80 an appropriate amount of the product of Example 77 was substituted for the product of Example 70 and an appropriate amount of phenylisocyanate was substituted for ethyl isocyanato acetate and the general procedure of Example 80 was followed the title compound was obtained. Total yield, 0.53 g (68%).

Anal for $C_{34}H_{35}N_3O_2$: Calcd: C, 78.89; H, 6.81; N, 8.12. Found: C, 78.49: H, 6.71; N, 8.00.

IR (KBr) 3290, 2963, 1683, 1674, 1669, 1642, 1540, 1500, 1446, 745 cm$^{-1}$.

EXAMPLE 89

N-(2,6-Diethylphenyl)-2-[[[(2,6-dimethylphenyl)amino]carbonyl](diphenylmethyl)amino]acetamide When in the procedure of Example 80 an appropriate amount of the product of Example 75 was substituted for the product of Example 70 and an appropriate amount of 2,6-dimethylphenylisocyanate was substituted for ethyl isocyanato acetate and the general procedure of Example 80 was followed the title compound was obtained. Total yield, 0.98 g (94%).

Anal for $C_{34}H_{37}N_3O_2$: Calcd: C, 78.58; H, 7.18; N, 8.09. Found: C, 78.32; H, 7.33; N, 8.04.

IR (KBr) 3352, 3349, 3296, 3286, 1655, 1647, 1639, 1601, 1519, 1515, 1451, 1306, 771, 698 cm$^{-1}$.

EXAMPLE 90

N-[2,6-bis(1-Methylethyl)phenyl]-2-[[[[4-(dimethylamino)phenyl]amino]thioxomethyl](phenylmethyl)amino]acetamide When in the procedure of Example 80 an appropriate amount of the product of Example 71 was substituted for the product of Example 70 and an appropriate amount of 4-dimethylaminophenylisothiocyanate was substituted for ethyl isocyanato acetate the title compound was obtained. Total yield, 0.84 g (80%).

Anal for $C_{30}H_{38}N_4OS$: Calcd: C, 71.68; H, 7.62; N, 11.15. Found: C, 71.74; H, 7.66; N, 10.89.

IR (KBr) 3247, 3226, 2959, 1683, 1663, 1473, 1338, 1209, 1200, 699 cm$^{-1}$.

EXAMPLE 91

N-[2,6-bis(1-Methylethyl)phenyl]-2-[[[[4-(dimethylamino)phenyl]amino]thioxomethyl](2,2-diphenylethyl)amino]acetamide When in the procedure of Example 80 an appropriate amount of 4-dimethylaminophenylisothiocyanate was substituted for ethyl isocyanato acetate and the general procedure of Example 80 was followed the title compound was obtained. Total yield, 1.15 g (70%).

Anal for $C_{37}H_{44}N_4OS$: Calcd: C, 74.96; H, 7.48; N, 9.45. Found: C, 74.93; H, 7.49; N, 9.08.

IR (KBr) 3256, 2962, 1665, 1538, 1523, 1180 cm$^{-1}$.

EXAMPLE 92

N-[2,6-bis(1-Methylethyl)phenyl]-2-[(diphenylmethyl)[[(4-methoxyphenyl)amino]thioxomethyl]-amino]acetamide When in the procedure of Example 80 an appropriate amount of 4-methoxyphenylisothiocyanate was substituted for ethyl isocyanato acetate and an appropriate amount of the product of Example 4 was substituted for the product of Example 70 and the general procedure of Example 80 was followed the title compound was obtained. Total yield, 1.69 g (80%).

Anal for $C_{35}H_{39}N_3O_2S$: Calcd: C, 74.30; H, 6.95; N, 7.43. Found: C, 73.66; H, 6.83; N, 7.09.

IR (KBr) 2964, 1662, 1513, 1497, 1361, 702 cm$^{-1}$.

EXAMPLE 93

N-[2,6-bis(1-Methylethyl)phenyl]-2-[[[[4-(dimethylamino)phenyl]amino]thioxomethyl](diphenylmethyl)amino]acetamide When in the procedure of Example 80 an appropriate amount of 4-dimethylaminophenylisothiocyanate was substituted for ethyl isocyanato acetate and an appropriate amount of the product of Example 4 was substituted for the product of Example 70 and the general procedure of Example 80 was followed the title compound was obtained. Total yield, 0.38 g (33%).

Anal for $C_{36}H_{42}N_4OS$: Calcd: C, 74.70; H, 7.31; N, 9.68. Found: C, 73.62; H, 7.28; N, 9.06.

IR (KBr) 3356, 2963, 1660, 1521, 1466, 1359, 1221, 703 cm$^{-1}$.

EXAMPLE 94

N-[2-[[2,6-bis(1-Methylethyl)phenyl]amino]-2-oxoethyl]-N-(diphenylmethyl)-2-methoxybenzamide 2-Methoxy benzoyl chloride (0.65 g) was added to a mixture of 1.50 g the product of Example 4 and excess triethylamine in 100 mL EtOAc. The reaction mixture was allowed to sit 2 days at room temperature and was then concentrated to dryness, the residue dissolved in 250 mL CH$_2$Cl$_2$, the organic solution washed with dilute sulfuric acid, brine, potassium carbonate solution, and brine. The solution was dried over MgSO$_4$, filtered, and concentrated to an oil which crystallized upon addition of 1/1, hexane/EtOAc to give the title compound. Total yield, 1.53 g (76%).

Anal for $C_{35}H_{38}N_2O_3$: Calcd: C, 78.62; H, 7.16; N, 5.24. Found: C, 77.39; H, 7.21; N, 4.73.

IR (KBr) 3272, 2962, 1615, 1601, 1463, 1245, 752 cm$^{-1}$.

EXAMPLE 95

4-[[[2-[[2,6-bis(1-Methylethyl)phenyl]amino]-2-oxoethyl](diphenylmethyl)amino]carbonyl]benzoic acid methyl ester When in the procedure of Example 94 an appropriate amount of 4-methoxycarbonylbenzoylchloride was substituted for 2-methoxycarbonylbenzoylchloride and the general procedure of Example 94 was followed the title compound was obtained. Total yield, 1.82 g (86%).

Anal for $C_{36}H_{38}N_2O_4$: Calcd: C, 76.84; H, 6.81; N, 4.98. Found: C, 75.81; H, 6.68; N, 4.56.

IR (KBr) 3359, 2964, 1725, 1689, 1635, 1505, 1435, 1277, 743 cm$^{-1}$.

EXAMPLE 96

N-[2[[2,6-bis(1-Methylethyl)phenyl]amino]-2-oxoethyl]-N-(diphenylmethyl)-2-(trifluoromethyl)benzamide When in the procedure of Example 94 an appropriate amount of 2-trifluoromethylbenzoyl chloride was substituted for 2-methoxybenzoyl chloride and the general procedure of Example 94 was followed the title compound was obtained. Total yield, 1.77 g (82%).

Anal for $C_{35}H_{35}N_2F_3O_2$: Calcd: C, 73,41; H, 6.16; N, 4.89. Found: C, 73.39; H, 6.23; N, 4.89.

IR (KBr) 3435, 2967, 2928, 1683, 1630, 1508, 1399, 1315, 1171, 755 cm$^{-1}$.

EXAMPLE 97

N-[2-[[2,6-bis(1-Methylethyl)phenyl]amino]-2-oxoethyl]-N-(diphenylmethyl)-2,2,3,3,4,4,4-heptafluorobutanamide When in the procedure of Example 79 an appropriate amount of the product of Example 4 was substituted for the product of Example 5 and an appropriate amount of heptafluorobutyric anhydride was substituted for acetic anhydride and the general procedure of Example 79 was followed the title compound was obtained. Total yield, 1.33 g (59%).

Anal for $C_{31}H_{31}F_7N_2O_2$: Calcd: C, 62.41; H, 5.24; N, 4.70. Found: C, 61.72; H, 5.11; N, 4.27.

IR (KBr) 3340, 1703, 1687, 1659, 1497, 1232, 1217, 700 cm$^{-1}$.

EXAMPLE 98

N-[2-[[2,6-bis(1-Methylethyl)phenyl]amino]-2-oxoethyl]-N-(diphenylmethyl)-4-nitro benzamide When in the procedure of Example 94 an appropriate amount of 4-nitrobenzoylchloride was substituted for 2-methoxybenzoyl chloride and the general procedure of Example 94 was followed the title compound was obtained. Total yield, 1.60 g (78%).

Anal for $C_{34}H_{35}N_3O_4$: Calcd: C, 74.29; H, 6.42; N, 7.64. Found: C, 74.28; H, 6.38; N, 7.36.

IR (KBr) 3352, 2965, 1684, 1637, 1523, 1507, 1352, 1313, 862, 701.

EXAMPLE 99

N-[2-[[2,6-bis(1-Methylethyl)phenyl]amino]-2-oxoethyl]-N-(diphenylmethyl)-2,5-dimethoxy benzamide When in the procedure of Example 94 an appropriate amount of 2,6-dimethoxybenzoyl chloride was substituted 2-methoxybenzoyl chloride and the general procedure of Example 94 was followed the title compound was obtained. Total yield, 1.69 g (80%).

Anal for $C_{36}H_{40}N_2O_4$: Calcd: C, 76.57; H, 7.14; N, 4.96. Found: C, 76.72; H, 7.14; N, 4.65.

IR (KBr) 3392, 2967, 1680, 1653, 1641, 1500, 1432, 1222, 1038, 749 cm$^{-1}$.

EXAMPLE 100

N-[2-[(2,6-Diethylphenyl)amino]-2-oxoethyl]-N-(diphenylmethyl)benzamide

When in the procedure of Example 94 an appropriate amount of the product of Example 75 was substituted for the product of Example 4 and an appropriate amount of 2,5-dimethoxybenzoyl chloride was substituted for 2-methoxybenzoyl chloride and the general procedure of Example 94 was followed the title compound was obtained. Total yield, 0.35 g (51%).

Anal for $C_{32}H_{32}N_2O_2$: Calcd: C, 80.64; H, 6.66; N, 5.88. Found: C, 80.29; H, 6.66; N, 5.79.

IR (KBr) 3304, 3029, 2966, 1695, 1672, 1640, 1601, 1539, 1521, 1448, 1223, 752, 740 cm$^{-1}$.

EXAMPLE 101

4-[[2-[[2,6-bis(1-Methylethyl)phenyl]amino]-2-oxoethyl]-(2,2-diphenylethyl)amino]-4-oxobutanoic acid When in the procedure of Example 78 an appropriate amount of the product of Example 70 was substituted for the product of Example 71 and the general procedure of Example 78 was followed the title compound was obtained. Total yield, 0.74 g (79%). Total yield, 0.74 g (79%).

Anal for $C_{32}H_{38}N_2O_4$: Calcd: C, 74,68; H, 7.44; N, 5.44. Found: C, 72.45; H, 7.40; N, 4.99.

IR (KBr) 3271, 3264, 2962, 1721, 1702, 1696, 1652, 1637, 1451, 1178, 701 cm$^{-1}$.

EXAMPLE 102

N-[2-[[2,6-bis(1-Methylethyl)phenyl]amino]-2-oxoethyl]-N-(9H-fluoren-9-yl)benzamide When in the procedure of Example 94 an appropriate amount of product of Example 77 was substituted for the product of Example 4 and an appropriate amount of benzoyl chloride was substituted for 2-methoxybenzoyl chloride and the general procedure of Example 94 was followed the title compound was obtained. Total yield, 0.56 g (76%).

Anal for $C_{34}H_{34}N_2O_2$: Calcd: C, 81.24; H, 6.82; N, 5.57. Found: C, 80.54; H, 6.95; N, 5.17.

IR (KBr) 3357, 2936, 1691, 1631, 1601, 1501, 1453, 1399, 1217, 750, 742 cm$^{-1}$.

EXAMPLE 103

N-[2,6-bis(1-Methylethyl)phenyl]-2-[bis(phenylmethyl)amino]acetamide

The product from Example 71 (0.72 g) was mixed with 0.42 g benzyl bromide, and excess triethylamine in 50 mL EtOAc and then heated on the steambath 2 hours. The reaction mixture was concentrated to dryness, the residue taken up in EtOAc, the solution filtered and then concentrated to a white solid. The solid was purified by chromatography on silica gel (70–230 mesh) using hexane/EtOAc, 1/1, as eluant. The product was obtained as a white solid. Total yield, 0.33 g (36%).

Anal for $C_{28}H_{34}N_2O$: Calcd: C, 81.12; H, 8.27; N, 6.75. Found: C, 80.94; H, 8.36; N, 6.40.

IR (KBr) 3317, 2966, 2833, 1667, 1494, 1486, 1473, 702 cm$^{-1}$.

EXAMPLE 104

N-[2-[[2,6-bis(1-Methylethyl)phenyl]amino]-2-oxoethyl]-N-(phenylmethyl)glycine, ethyl ester When in the procedure of Example 103 an appropriate amount of bromoacetic acid ethyl ester was substituted for benzylbromide and the general procedure of Example 103 was followed the title compound was obtained. Total yield, 0.64 g (50%).

Anal for $C_{25}H_{34}N_2O_3$: Calcd: C, 73.14; H, 8.35; N, 6.82. Found: C, 73.17; H, 8.47; N, 6.55.

IR (KBr) 3277, 2967, 1730, 1678, 1496, 1204, 799 cm$^{-1}$.

EXAMPLE 105

[2-[[2,6-bis(1-Methylethyl)phenyl]amino]-2-oxoethyl](9H-fluoren-9-yl)carbamic acid, phenyl ester When in the procedure of Example 94 an appropriate amount of the product of Example 77 was substituted for the product of Example 4 and an appropriate amount of phenoxycarbonyl chloride was substituted for 2-methoxybenzoyl chloride and the general procedure of Example 94 was followed the title compound was obtained. Total yield, 0.94 g (82%).

Anal for $C_{34}H_{34}N_2O_3$: Calcd: C, 78.74; H, 6.61; N, 5.40. Found: C, 78.87; H, 6.70; N, 5.30.

IR (KBr) 3313, 1714, 1701, 1685, 1653, 1507, 1442, 1383, 1202, 744 cm$^{-1}$.

EXAMPLE 106

N-(2,6-Diethylphenyl)-2-[[[[4-(dimethylamino)phenyl]amino]thioxomethyl](diphenylmethyl)amino]acetamide When in the procedure of Example 80 an appropriate amount of 4-dimethylaminophenylisothiocyanate was substituted for ethyl isocyanato acetate and an appropriate amount of the product of Example 4 was substituted for the product of Example 70 and the general procedure of Example 80 was followed the title compound was obtained. Total yield, 0.68 g (62%).

Anal for $C_{34}H_{38}N_4OS$: Calcd: C, 74.15; H, 6.95; N, 10.17. Found: C, 76.21; H, 6.98; N, 8.98.

IR (KBr) 3233, 1652, 1539, 1522, 1509, 1362, 702 cm$^{-1}$.

EXAMPLE 107

1,1-Dimethylethyl-[2-[2,6-bis-(1-methylethyl)phenyl]amino]-2-oxoethyl]carbamate

Employing the method of Example 20, but using an appropriate amount of N-boc-glysine instead of N-boc-O-benzyl-(L)-tyrosine, the title compound was prepared, mp 130°–135° C.

EXAMPLE 108

(S)-N-[2,6-bis(1-Methylethyl)phenyl]-α-[-(phenylmethyl)amino]benzenepropanamide

A solution of (S)-α-amino-N-[2,6-bis(1-Methylethyl)phenyl]benzenepropanamide (1.0 g, 3.1 mmol) and benzaldehyde (0.33 g, 3.1 mmol) in toluene (100 mL) was heated under reflux for 1 hour with the azeotropic removal of water then cooled (25° C.). To the resulting solution was added one equivalent of Raney nickel, and the resulting slurry was shaken vigorously under hydrogen (53 psi, 82 min 25° C.). The resulting slurry was filtered, and the filtrate was concentrated. The resulting oil was triturated with ether/hexane (1:1), and the resulting precipitate was collected by filtration to yield 0.27 g (21%) of the title compound, mp 120°–124° C.

EXAMPLE 109

(S)-N-[2,6-bis(1-Methylethyl)phenyl]-4-(phenylmethoxy)-α-[(phenylmethyl)amino]benzenepropanamide A solution of (S)-α-amino-4-(phenylmethoxy)-N-(2,4,6-trifluorophenyl)benzenepropanamide (1.0 g, 2.3 mmol) and benzaldehyde (0.25 g, 2.3 mmol) in toluene was heated under reflux with the azeotropic removal of water (1 hr). The resulting solution was cooled (25° C.), then methanol (30 mL) and an excess of sodium borohydride was added, and the resulting slurry was stirred (2h, 25° C.). To the resulting mixture was added 3% aqueous H₂O₂ (ca. 10 mL), and the resulting mixture was again stirred (1 hr, 25° C.). The resulting mixture was diluted with ethyl acetate (200 mL), washed with water (2×100 mL), washed with brine (1×100 mL), then dried (MgSO₄) and concentrated. The resulting oil was triturated with ether:hexane (1:1) and the resulting precipitate was collected by filtration to yield 0.11 g (9.1%) of the title compound, mp 127°–129° C.

EXAMPLE 110

(±)-1,1-Dimethylethyl-[2-[[2,6-bis(1-methylethyl)-phenyl]amino]-2-oxo-1-phenylmethyl)ethyl]methylcarbamate Employing the method of Example 20, but using an appropriate amount of (±)-N-boc-N-methylphenylalanine instead of N-boc-O-benzyl-(L)-tyrosine, the title compound was prepared, mp 90°–92° C.

Anal for $C_{27}H_{38}N_2O_3$: Calcd: C, 73.94; H, 8.73; H, 6.39. Found: C, 73.92; H, 8.52, N, 6.20.

EXAMPLE 111

(S)-1,1-Dimethylethyl-[2-[[2,6-bis(1-methylethyl)phenyl ]amino]-2-oxo-1-phenylmethyl)ethyl]methyl carbamate Employing the method of Example 20, but using an appropriate amount of (S)-N-boc-N-methylphenylalanine instead of N-boc-O-benzyl-(L)-tyrosine, the title compound was prepared as an oil.

¹H NMR (250 MHz, CDCl₃) δ 7.51 (S, 1H), 7.2 (m, 8H), 5.07 (dd, 1H), 3.43 (dd, 1H), 2.98 (dd, 1H), 2.90 (S, 3H), 2.76 (m, 2H), 1.48 (S, 9H), 1.08 (d, 6H), and 1.04 (d, 6H).

EXAMPLE 112

(S)-[1-[[[2,6-bis(1-Methylethyl)phenyl]amino]carbonyl]-3-phenylpropyl]-carbamic acid, 1,1-dimethylethyl ester Employing the method of Example 20, but using a appropriate amount of (S)-N-boc-α-amino-4-phenylbutanoic acid instead of N-boc-O-benzyl-(L)-tyrosine, the title compound was prepared, mp 193°–197° C.

EXAMPLE 113

(S)-2-Amino-N-[2,6-bis(1-methylethyl)phenyl]propanamide

Employing the method of Example 22, but using an appropriate amount of (S)-[2-[2,6-bis(1-Methylethyl)-phenyl]-amino]-1-methylethyl]carbamic acid, 1,1-dimethylethyl ester instead of (S)-1,1-dimethylethyl-[2-[2,6-bis(1-Methylethyl)phenyl]amino]-2-oxo-1-[4-(phenylmethoxy)phenyl]methyl]ethyl]carbamate, the title compound was prepared, mp 118.5°–121.5° C.

EXAMPLE 114

(S)-N-[2,6-bis(1-Methylethyl)phenyl]-2-[(diphenylmethyl)amino]propanamide

A solution of (S)-2-amino-N-[2,6-bis(1-Methylethyl)-phenyl]propanamide (5.0 g, 20 mmol), benzhydryl bromide (5.0 g, 20 mmol), and triethylamine (2.8 mL, 20 mmol) in acetonitrile (100 mL) was heated under reflux for 5 hours. The resulting solution was cooled (25° C.) and concentrated in vacuo. The residue was taken up in ethyl acetate (300 mL), washed with water (1×100 mL), washed with saturated sodium bicarbonate (1×100 mL), washed with brine (1×100 mL), then dried (MgSO₄) and concentrated in vacuo. The resulting solid was recrystallized from ether/hexane to yield 4.77 g (57.1%) of the title compound as fine white needles, mp 134°–138.5° C.

EXAMPLE 115

(S)-N-[2-[2,6-bis(1-Methylethyl)phenyl]amino]-1-methyl-2-oxoethyl]-α-phenylbenzeneacetamide A solution of diphenylacetyl chloride (0.93 g, 4.0 mmol) in THF (5 mL) was added to a cooled (0° C.) solution of (S)-2-amino-N-[2,6-bis(1-Methylethyl)-phenyl]propanamide (1.0 g, 4.0 mmol) and triethylamine (0.56 mL, 4.0 mmol) in THF (20 mL) dropwise via pipet. The ice bath was removed and the resulting slurry was stirred (1 hr, 25° C.). The resulting slurry was diluted with dichloromethane (200 mL), washed with 1N HCl (2×65 mL), washed with brine (1×69 mL), washed with saturated sodium bicarbonate (1×65 mL), again with brine (1×65 mL) then dried (MgSO₄) and concentrated in vacuo. The resulting solid was recrystallized from ethyl acetate to yield 1.36 g (76.3%) of the title compound as a white solid, mp 264°–265.5° C.

EXAMPLE 116

(S)-[2-[[2,6-bis(1-Methylethyl)phenyl]amino]-2-oxo-1-[[4-(phenylmethoxy)phenyl]methyl]ethyl]carbamic acid, methyl ester To a coded (0° C.) solution of (S)-α-amino-N-[2,6-bis(1-Methylethyl)phenyl]-4-(phenylmethoxy)benzenepropanamide (4.50 g, 10.5 mmol) and triethylamine (1.75 mL, 12.5 mmol) in THF (125 mL) was added methylchloroformate (0.97 mL, 12.5 mmol). The resulting slurry was stirred (1 hr, 0° C.) then filtered, and the filtrate was concentrated. The residue was taken up in ethyl acetate (300 mL), washed with water (1×mL), washed with saturated sodium bicarbonate (1×100 mL), washed with brine (1×100 mL), then dried (MgSO₄) and concentrated in vacuo. The resulting solid was recrystallized from ethyl acetate to yield 3.0 g (59%) of the title compound, mp 179°–182° C.

EXAMPLE 117

(S)-N-[2,6-bis(1-Methylethyl)phenyl]-α-(dimethylamino)-4-(phenylmethoxy)benezenepropanamide A solution of (S)-α-amino-N-[2,6-bis(1-Methylethyl)-phenyl]-4-(phenylmethoxy)benzenepropanamide (3.0 g, 7.0 mmol), 30% aqueous formaldehyde (2.1 mL, 21 mmol), and sodium cyanoborohydride (0.88 g, 14 mmol) in ethanol (100 mL) was stirred at room temperature (3 hr) and, using bromocresol green as an indicator, was maintained at a blue-green endpoint by adding 1.0N aqueous HCl. The resulting mixture was concentrated. The residue was taken up in ethyl acetate (300 mL), washed with saturated sodium bicarbonate (1×100 mL), washed with brine (1×100 mL), then dried (MgSO₄) and concentrated in vacuo. The resulting oil was crystallized by triturating with ether/hexane to yield 2.3 g (72%) of the title compound, mp 103°–107° C.

EXAMPLE 118

(S)-N-[2,6-bis(1-Methylethyl)phenyl-α-[(diphenylmethyl)amino]-4-(phenylmethoxy)benzenepropanamide Employing the method of Example 114 but using an appropriate amount of (S)-α-amino-N-[2,6-bis(1-

Methylethyl)phenyl]-4-(phenylmethoxy)benzenepropanamide instead of (S)-2-amino-N-[2,6-bis(1-Methylethyl)phenyl]propanamide, the title compound was prepared, mp 148.5°-150° C.

EXAMPLE 119

(S)-[2-[[2,6-bis(1-Methylethyl)phenyl]amino]-1-methyl-2-oxoethyl]methylcarbamic acid, 1,1-dimethylethyl ester Employing the method of Example 20, but using an appropriate amount of N-boc-N-methyl-(L)-alanine instead of N-boc-O-benzyl-(L)-tyrosine, the title compound was prepared, mp 108°-110° C.

EXAMPLE 120

(S)-[2-Oxo-1-[[4-(phenylmethoxy)phenyl]methyl]-2-[(2,4,6-trimethoxyphenyl)amino]ethyl]carbamic acid, 1,1-dimethylethyl ester Employing the method of Example 20, but using an appropriate amount of a mixture of 2,4,6-trimethoxyaniline hydrochloride and triethyl amine instead of 2,6-diisopropylaniline, the title compound was prepared, mp 89°-95° C.

EXAMPLE 121

(S)-[1-(1H-Indol-3-ylmethyl)-2-oxo-2-[2,4,6-trimethoxyphenyl)amino]ethyl]carbamic acid, 1,1-dimethylethyl ester Employing the method of Example 20, but using an appropriate amount of N-boc-(L)-tryptophan instead of N-boc-O-benzyl-(L)-tyrosine and using a mixture of 2,4,6-trimethoxyaniline hydrochloride and triethylamine instead of 2,6-diisopropylaniline, the title compound was prepared, mp 89.5°-97.5° C.

EXAMPLE 122

(±)-N-[2,6-bis(1-Methylethyl)phenyl]-2-[(2-naphthalenyl)phenylmethyl]aminoacetamide N-[2,6-bis(1-Methylethyl)phenyl]-2-bromoacetamide (1.1 g, 3.4 mmol) was added to a solution of triethylamine (0.6 mL, 4.2 mmol) and amino(2-naphthyl)phenylmethane (1.0 g, 4.2 mmol) in toluene (10 mL). The mixture was heated at reflux for 3 hours. After cooling and filtration, the filtrate was concentrated. Flash chromatography on silica gel (3:7 ethyl acetate/hexane) provided 1.4 g of a white foam, which was recrystallized (ethyl acetate/hexane) to afford 1.0 g (69%) of the product as a white solid, mp 146°-148° C.

IR (KBr) 3248, 2962, 1656, 1507, 1493, 1452, 816, 747, 701 cm$^{-1}$; $^1$H NMR (250 MHz, CDCl$_3$) δ 8.61 (s, 1H), 7.90-7.77 (m, 4H), 7.50-7.15 (m, 11H), 5.12 (s, 1H), 3.56 (s, 2H), 3.02 (m, 2H), 2.48 (brs, 1H), 1.20 (d, 12H).

Anal for $C_{31}H_{34}N_2O$: Calcd: C, 82.63; H, 7.60; N, 6.22. Found: C, 82.32; H, 7.63; N, 5.98.

EXAMPLE 123

(±)-N-[2,6-bis(1-Methylethyl)phenyl]-2-[(4-bromophenyl)phenylmethyl]aminoacetamide Employing the method of Example 122, but using an appropriate amount of amino (4-bromophenyl)phenylmethane instead of amino(2-naphthyl)phenylmethane, the title compound was prepared, mp 154°-155° C.

EXAMPLE 124

(±)-N-[2,6-bis(1-Methylethyl)phenyl]-2-[(4-methoxyphenyl)phenylmethyl]aminoacetamide Employing the method of Example 122, but using an appropriate amount of amino(4-methoxyphenyl)phenylmethane instead of amino(2-naphthyl)phenylmethane, the title compound was prepared, mp 117°-118° C.

EXAMPLE 125

(±)-N-[2,6-bis(1-Methylethyl)phenyl]-2-[phenyl(2-thienyl)methyl]aminoacetamide

Employing the method of Example 122, but using an appropriate amount of aminophenyl(2-thienyl)methane instead of amino[2-naphthyl)phenyl(methane, the title compound was prepared, mp 164°-166° C.

EXAMPLE 126

(±)-N-[2,6-bis(1-Methylethyl)phenyl]-2-[phenyl(2-pyridinyl)methyl]aminoacetamide Employing the method of Example 122, but using an appropriate amount of aminophenyl(2-pyridinyl) methane instead of amino(2-naphthyl)phenylmethane, the title compound was prepared, mp 135°-136° C.

EXAMPLE 127

(±)-N-[2,6-bis(1-Methylethyl)phenyl]-2-[(1-naphthalenyl)phenylmethyl]aminoacetamide Employing the method of Example 122, but using an appropriate amount of amino(1-naphthyl)phenylmethane instead of amino(2-naphthyl)phenylmethane, the title compound was prepared, mp 149°-151° C.

EXAMPLE 128

(±)-N-[2,6-bis(1-Methylethyl)phenyl]-2-[bis(2-pyridinyl)methyl]aminoacetamide

Employing the method of Example 122, but using an appropriate amount of amino-bis(2-pyridinyl)methane instead of amino(2-naphthyl)phenylmethane, the title compound was prepared, mp 134°-135° C.

EXAMPLE 129

(±)-N-[2,6-bis(1-Methylethyl)phenyl]-2-[[4-(dimethylamino)phenyl]phenylmethyl]aminoacetamide Employing the method of Example 122, but using an appropriate amount of amino[4-(dimethylamino)phenyl]phenylmethane instead of amino (2-naphthyl)phenylmethane, the title compound was prepared, mp 116°-117° C.

EXAMPLE 130

(±)-N-[2,6-bis(1-Methylethyl)phenyl]-2-[(4-hydroxyphenyl)phenylmethyl]aminoacetamide Employing the method of Example 122, but using an appropriate amount of amino(4-hydroxyphenyl)phenylmethane instead of amino(2-naphthyl)phenylmethane, the title compound was prepared, mp 190°-192° C.

EXAMPLE 131

(S)-N-[2,6-bis(1-Methylethyl)phenyl]-2-[1-[(1-naphthalenyl)ethyl]amino]acetamide Employing the method of Example 122, but using an appropriate amount of (S)-1-(1-naphthyl)ethylamine instead of amino(2-naphthyl)phenylmethane, the title compound was prepared, mp 154°-155° C. $[\alpha]_d^{23} = -8.6°$ C. (1.08%, CHCl$_3$).

EXAMPLE 132

(R)-N-[2,6-bis(1-Methylethyl)phenyl]-2-[1-[(1-naphthalenyl)ethyl]amino]acetamide Employing the method of Example 122, but using an appropriate amount of (R)-1-(1-naphthyl)ethylamine instead of amino(2-naphthyl)phenylmethane, the title compound was prepared, mp 153°-155° C., $[\alpha]_d^{23} = +8.8$, (1.0%, CHCl$_3$).

EXAMPLE 133

(R)-N-[2,6-bis(1-Methylethyl)phenyl]-2-[(1-phenylethyl)amino]acetamide

Employing the method of Example 122, but using an appropriate amount of (R)-α-methylbenzylamine instead of amino(2-naphthyl)phenylmethane, the title compound was prepared, mp 119°-120° C., $[\alpha]_d^{23} = +34$ (1.1%, CHCl$_3$).

EXAMPLE 134

(S)-N-[2,6-bis(1-Methylethyl)phenyl]-2-[(1-phenylethyl)amino]acetamide

Employing the method of Example 122, but using an o appropriate amount of (S)-α-methyl benzylamine instead of amino(2-naphthyl)phenylmethane, the title compound was prepared, mp 120°-121° C., $[\alpha]_d^{23} = -36$ (1%, CHCl$_3$).

EXAMPLE 135

(±)-N-[2,6-bis(1-Methylethyl)phenyl]-2-[1-(2-methoxyphenyl)ethyl]aminoacetamide

Employing the method of Example 122, but using an appropriate amount of 1-(2-methoxyphenyl)ethylamine instead of amino(2-naphthyl)phenylmethane, the title compound was prepared, mp 68°-70° C.

EXAMPLE 136

(±)-N-[2,6-bis(1-Methylethyl)phenyl]-2-[1-(2-pyridinyl)ethyl]aminoacetamide

Employing the method of Example 122, but using an appropriate amount of 1-(2-pyridinyl)ethylamine instead of amino(2-naphthyl)phenylmethane, the title compound was prepared, mp 99°-101° C.

EXAMPLE 137

N-[2,6-bis(1-Methylethyl)phenyl]-2-[[bis(4-chlorophenyl)methylamino]acetamide

Employing the method of Example 122, but using an appropriate amount of amino bis(4-chlorophenyl)methane instead of amino(2-naphthyl)phenylmethane, the title compound was prepared, mp 180°-181° C.

EXAMPLE 138

(±)-N-[2,6-bis(1-Methylethyl)phenyl]-2-[[(4-fluorophenyl)phenylmethyl]amino]acetamide Employing the method of Example 122 but using an appropriate amount of amino(4-fluorophenyl)phenylmethane instead of amino(2-naphthyl)phenylmethane, the title compound was prepared, mp 161° C.

EXAMPLE 139

(±)-N-[2,6-bis(1-Methylethyl)phenyl]-2-[[(2-methoxyphenyl)phenylmethyl]amino]acetamide Employing the method of Example 122, but using an appropriate amount of amino(2-methoxyphenyl)phenylmethane instead of amino(2-naphthyl)phenylmethane, the title compound was prepared, mp 133°-134° C.

EXAMPLE 140

(±)-N-[2,6-bis(1-Methylethyl)phenyl]-2-[[(4-methylphenyl)phenylmethyl]amino]acetamide Employing the method of Example 122, but using an appropriate amount of amino(4-methylphenyl)phenylmethane instead of amino(2-naphthyl)phenylmethane, the title compound was prepared, mp 165°-166° C.

EXAMPLE 141

N-[2,6-bis(1-Methylethyl)phenyl]-2-[[bis(4-fluorophenyl)methyl]amino]acetamide

Employing the method of Example 122, but using an appropriate amount of amino-bis(4-fluorophenyl)methane instead of amino(2-naphthyl)phenylmethane, the title compound was prepared, mp 150°-151° C.

EXAMPLE 142

N-[2,6-bis(1-Methylethyl)phenyl]-2-[[bis(4-methoxyphenyl)methyl]amino]acetamide

Employing the method of Example 122, but using an appropriate amount of amino bis(4-methoxy phenyl)methane instead of amino(2-naphthyl)phenylmethane, the title compound was prepared, mp 84°-85° C.

EXAMPLE 143

(±)-N-[2,6-bis(1-Methylethyl)phenyl]-2-[[(3-methylphenyl)phenylmethyl]amino]acetamide Employing the method of Example 122, but using an appropriate amount of amino(3-methylphenyl)phenylmethane, instead of amino(2-naphthyl)phenylmethane, the title compound was prepared, mp 119°-120° C.

EXAMPLE 144

(±)-N-[2,6-bis(1-Methylethyl)phenyl]-2-[[(2-chlorophenyl)phenylmethyl]amino]acetamide Employing the method of Example 122, but using an appropriate amount of amino(2-chlorophenyl)phenylmethane instead of amino(2-naphthyl)phenylmethane, the title compound was prepared, mp 119°-121° C.

EXAMPLE 145

(±)-N-[2,6-bis(1-Methylethyl)phenyl]-2-[[(2-methylphenyl)phenylmethyl]amino]acetamide Employing the method of Example 122, but using an appropriate amount of amino(2-methylphenyl)phenylmethane instead of amino(2-naphthyl)phenylmethane, the title compound was prepared, mp 163°–164° C.

EXAMPLE 146

(±)-N-[2,6-bis(1-Methylethyl)phenyl]-2-[[(4-nitrophenyl)phenylmethyl]amino]acetamide Employing the method of Example 122, but using an appropriate amount of amino(4-nitrophenyl)phenylmethane instead of amino(2-naphthyl)phenylmethane, the title compound was prepared, mp 177°–179° C.

EXAMPLE 147

N-[2,6-bis(1-Methylethyl)phenyl]-2-[[bis(3-(trifluoromethyl)phenyl)methyl]amino]acetamide Employing the method of Example 122, but using an appropriate amount of amino-bis[3-(trifluoromethyl)phenyl]methane instead of amino(2-naphthyl)phenylmethane, the title compound was prepared, mp 144°–45° C.

EXAMPLE 148

(±)-N-[2,6-bis(1-Methylethyl)phenyl]-2-[[(3,5-dimethoxyphenyl)phenylmethyl]amino]acetamide Employing the method of Example 122, but using an appropriate amount of amino[3,5-dimethoxyphenyl]phenylmethane instead of amino(2-naphthyl)phenylmethane, the title compound was prepared, mp 111°–112° C.

EXAMPLE 149

(±)-3-[[[2-[[2,6-bis(1-Methylethyl)phenyl]amino]-2-oxoethyl]amino]phenylmethyl]benzoic acid methyl ester Employing the method of Example 122, but using an appropriate amount of 3-(aminophenylmethyl)benzoicacidmethyl ester instead of amino(2-naphthyl)phenylmethane the title compound was prepared, mp 131°–132° C.

EXAMPLE 150

(±)-N-[2,6-bis(1-Methylethyl)phenyl]-2-[[[3-(hydroxymethyl)phenyl]phenylmethyl]amino]acetamide The title compound was prepared by the reduction of the product of Example 149 by LiAlH$_4$ at room temperature, mp 57°–62° C.

EXAMPLE 151

(±)-3-[[[2-[[2,6-bis(1-Methylethyl)phenyl]amino]-2-oxoethyl]amino]phenylmethyl]benzoic acid The title compound was prepared by the hydrolysis of the product of Example 149 by NaOH in aqueous methanol, mp 190°–191° C.

EXAMPLE 152

(±)-4-[[[2-[[2,6-bis(1-Methylethyl)phenyl]amino]-2-oxoethyl]amino]phenylmethyl]benzoic acid ethyl ester Employing the method of Example 122, but using an appropriate amount of 4-(aminophenylmethyl)benzoic acid ethyl ester instead of amino(2-naphthyl)phenylmethane, the title compound was prepared, mp 139°–140° C.

EXAMPLE 153

(±)-4-[[[2-[[2,6-bis(1-Methylethyl)phenyl]amino]-2-oxoethyl]amino]phenylmethyl]benzoic acid The title compound was prepared by the hydrolysis of the product of Example 152 by NaOH in aqueous methanol, mp 245°–246° C.

EXAMPLE 154

(±)-N-[2,6-bis(1-Methylethyl)phenyl]-2-[[(3,5-dimethoxyphenyl)(2-methylphenyl)methyl]amino]acetamide Employing the method of Example 122, but using an appropriate amount of amino(3,5-dimethoxyphenyl)(2-methylphenyl)methane instead of amino(2-naphthyl)phenylmethane, the title compound was prepared, mp 138°–139° C.

EXAMPLE 155

(±)-2-[Acetyl[(3,5-dimethoxylphenyl)(2-methylphenyl)methyl]amino]-N-[2,6-bis(1-Methylethyl)phenyl]acetamide To a well-stirred solution of (±)-N-[2,6-[bis(1-methylethyl)phenyl]-2-[(3,5-dimethoxy)(2-methylphenyl)methyl]amino]acetamide (0.48 g, 1.0 mmol), triethylamine (0.1 g, 1.0 mmol) in toluene (20 mL) was added acetyl chloride (0.08 g, 1.0 mmol). The resulting slurry was stirred for 30 minutes and filtered. It was diluted with ethyl acetate (50 mL) and washed with brine (1×50 mL), saturated sodium bicarbonate (1×50 mL), with brine again (1×50 mL), then dried (MgSO$_4$) and concentrated. Flash chromatography on silica gel (1:1 ethyl acetate/hexane) provided 0.45 g of white solid, which was recrystallized (ethyl acetate/hexane) to afford 0.33 g (64%) of product, mp 142°–145° C.

EXAMPLE 156

N-[2,6-bis(1-Methylethyl)phenyl]-(±)-[(2,2-diphenylethyl)amino]benzeneacetamide

When in the procedure of Example 39, Step 2, an appropriate amount of 2,2-diphenylethylamine was substituted for benzyl amine and the general procedure of Example 39 was followed the title compound was obtained, mp 174°–176° C.

EXAMPLE 157

N-[2,6-bis(1-Methylethyl)phenyl]-(±)-[(2-phenylethyl)amino]benzeneacetamide

When in the procedure of Example 39, Step 2, an appropriate amount of phenylethylamine was substituted for benzylamine and the general procedure of Example 39 was followed the title compound was obtained, mp 120°–123° C.

EXAMPLE 158

N-[2,6-bis(1-Methylethyl)phenyl]-(±)-(hexylamino)benzeneacetamide

When in the procedure of Example 39, Step 2, an appropriate amount of hexylamine was substituted for benzylamine and the general procedure of Example 39 was followed the title compound was obtained, mp 110°–112° C.

EXAMPLE 159

N-[2,6-bis(1-Methylethyl)phenyl]-2-bromoacetamide

Bromoacetyl bromide (17.0 g, 84.6 mmol) was added dropwise to a well-stirred ice cold solution of 2,6-diisopropylaniline (10.0 g, 56.4 mmol) in acetone (25 mL) and water (25 mL) containing sodium acetate (15.3 g, 112.8 mmol). The reaction mixture was stirred at room temperature for an hour and then diluted with water (100 mL). The product was filtered and washed with cold water, saturated sodium, bicarbonate, again with water, and finally with hexane. It was dried in a vacuum at 40° C. to yield 14.5 g (86%) of title compound as a white solid $^1$H NMR was consistent with the title compound.

When in the procedure of Example 159 an appropriate amount of α-bromophenylacetyl bromide was substituted for bromoacetyl bromide and the general procedure of Example 159 is followed, N-[2,6-bis (1-methylethyl)phenyl]-2-bromophenylacetamide was obtained.

CHART I

Scheme 1:

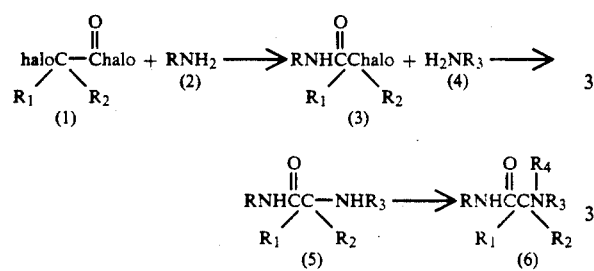

Scheme 2:

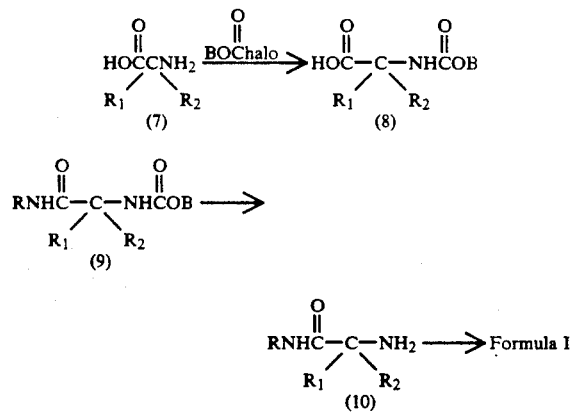

Chart II

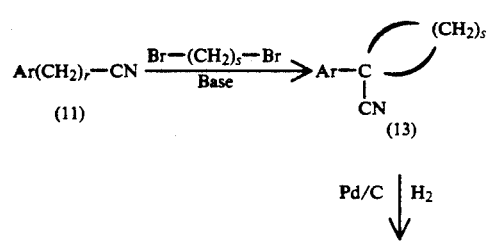

-continued
Chart II

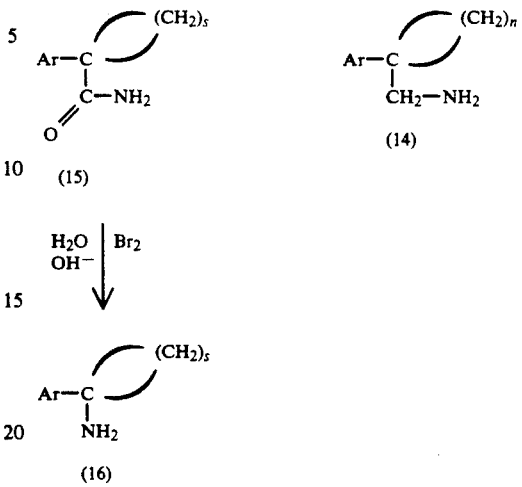

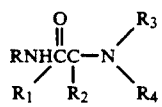

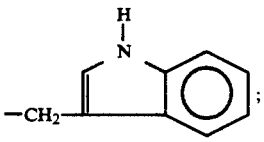

We claim:

1. A method of treating hypocholesterolemia and atherosclerosis comprising administering to a patient an effective amount of a compound of the formula $$\underset{R_1 \quad R_2}{RNHCC}\underset{}{\overset{O}{\|}}\underset{}{-}N\underset{R_4}{\overset{R_3}{\diagup}}$$

wherein R is phenyl $(CH_2)_n$— wherein n is zero and wherein the phenyl ring is substituted with two substituents in the 2- and 6-positions of the phenyl ring or with three substituents in the 2-, 4-, and 6-positions of the phenyl ring said substituents being selected from alkyl having 1 to 6 carbon atoms and which is straight or branched, alkoxy having from 1 to 6 carbon atoms and which is straight or branched, fluorine, chlorine, or bromine;

wherein $R_1$ is
  (a) hydrogen, or
  (b) alkyl having from 1 to 6 carbon atoms and is straight or branched;

wherein $R_2$ is
  (a) hydrogen;
  (b) a straight or branched hydrocarbon chain having from 1 to 20 carbon atoms and which is saturated or contains from 1 to 3 double bonds;
  (c) p-phenylmethoxybenzyl;
  (d)

![indole-CH2 structure]

(e) —$CH_2CH_2S(O)_{0-2}CH_3$; or
  (f) phenyl, 1- or 2-naphthyl which is unsubstituted or is substituted with one or two substituents selected from alkyl having from 1 to 4 carbon atoms and which is straight or branched, alkoxy having from 1 to 4 carbon atoms, hydroxy, chlorine, fluorine, bromine, trifluoromethyl, or amino;

(g) the group

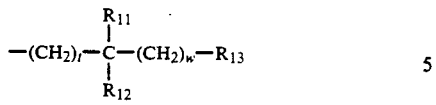

wherein t is zero to 4; w is zero to 4 with the proviso that the sum of t and w is not greater than 5; $R_{11}$ and $R_{12}$ are independently selected from hydrogen or alkyl having from 1 to 6 carbon atoms, or when $R_{11}$ is hydrogen, $R_{12}$ can be selected from the groups defined for $R_{13}$; and $R_{13}$ is phenyl, 1- or 2-naphthyl, or phenyl 1- or 2-naphthyl substituted with from one to three substituents selected from straight or branched alkyl having from 1 to 6 carbon atoms, straight or branched alkoxy having from 1 to 6 carbon atoms, phenoxy, hydroxy, fluorine, chlorine, bromine, nitro, hydroxymethyl, trifluoromethyl, —COOH, COOalkyl wherein alkyl has from 1 to 4 carbon atoms, and is straight or branched, —$NR_5R_6$ wherein $R_5$ and $R_6$ are independently hydrogen or straight or branched alkyl of from 1 to 4 carbon atoms, or —$CH_2NR_5R_6$ wherein $R_5$ and $R_6$ have the meanings defined above:

(h) $R_1$ and $R_2$ taken together with the carbon atom to which they are attached form a saturated carbocyclic ring having from 3 to 7 carbon atoms;

$R_3$ is
(a) hydrogen
(b) a straight or branched hydrocarbon chain having from 1 to 20 carbon atoms and which is saturated or contains from 1 t 3 double bonds;
(c) the group

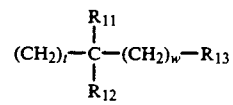

wherein q is zero to 3; r is zero to 2; s is 2 to 6; and Ar is
phenyl,
1- or 2-naphthyl,
phenyl or 1- or 2-naphthyl substituted with straight or branched alkyl of from 1 to 6 carbon atoms,
straight or branched alkoxy of from 1 to 6 carbon atoms,
hydroxy,
benzyloxy,
fluorine,
chlorine,
bromine,
nitro,
trifluoromethyl,
—NH—$COCH_3$,
—$CONH_2$,
—COOH,
—$CH_2COOH$,
—$CH_2CONH_2$,
—$NR_7R_8$ wherein
$R_7$ and $R_8$ are independently hydrogen, alkyl of from 1 to 6 carbon atoms the terminal carbon of which optionally is substituted with an $OR_9$ group where $R_9$ is hydrogen, alkyl of from 1 to 6 carbon atoms, alkanoyl having from 2 to 5 carbon atoms, benzoyl, or $R_7$ and $R_8$ taken together with the nitrogen atom to which they are attached from a 5- or 6-membered ring optionally interrupted by an oxygen atom or —$NR_9$; wherein $R_9$ is as defined above;
—$CH_2NR_7R_8$ where $R_7$ and $R_8$ are as defined above;
—$CH_2OR_9$ where $R_9$ is as defined above;
—COO-alkyl where alkyl is from 1 to 6 carbons and is straight or branched and the terminal carbon of which optionally is substituted with an $OR_9$ group or $NR_7R_8$ where $R_7$, $R_8$, and $R_9$ are as defined above;
—$NHCH_2COO$-alkyl where alkyl is from 1 to 4 carbon atoms and is straight or branched;
—$SO_2NR_7R_8$ where $R_7$ and $R_8$ are as defined above;
—$SO_2OR_9$ where $R_9$ is as defined above, or
—NH—$SO_2R_{10}$ where $R_{10}$ is alkyl of 1 to 4 carbon atoms or phenyl;
(d) the group

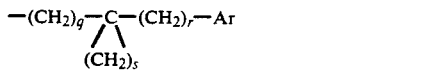

wherein t, w, $R_{11}$, $R_{12}$, and $R_{13}$ have the meanings defined hereinabove; or
(e) 9-fluorenyl, 9-fluorenyl mono-substituted or disubstituted with chlorine, fluorine or bromine; or 9-fluorenyl mono-substituted on the 1-, 2-, or 4-position with straight or branched alkyl having from 1 to 6 carbon atoms, straight or branched alkoxy having from 1 to 6 carbon atoms, hydroxy, hydroxymethyl, —COOH, —COOalkyl wherein the alkyl group is straight or branched and has from 1 to 6 carbon atoms, or —$CONR_5R_6$ wherein $R_5$ and $R_6$ have the meaning defined above;

$R_4$ is
(a) hydrogen;
(b) a straight or branched hydrocarbon chain having from 3 to 20 carbon atoms and which is saturated or contains from 1 to 3 double bonds;
(c) the group

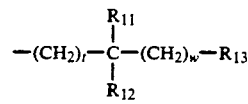

wherein t, w, $R_{11}$, $R_{12}$, and $R_{13}$ have the meanings defined hereinabove;
(d) or $R_3$ is hydrogen or a saturated straight hydrocarbon chain having from 1 to 4 carbon atoms and $R_4$ is trityl;
(e) 9-fluorenyl or 9-fluorenyl substituted with from 1 to 3 substituents selected from fluorine, chlorine, bromine, straight or branched alkyl having from 1 to 4 carbon atoms; —NHCO alkyl or —$CO_2$ alkyl wherein alkyl has from 1 to 4 carbon atoms and is straight or branched; or
(f) phenyl or phenyl substituted with one or two substituents selected from straight or branched alkyl having from 1 to 4 carbon atoms, chlorine, bromine, fluorine, trifluoromethyl, hydroxy, straight or branched alkoxy having from 1 to 4 carbon atoms, amino or nitro; or a pharmaceutically acceptable salt thereof; with the provisos that each of $R_1$, $R_2$, $R_3$, and $R_4$ is not hydrogen at the same time; each of $R_2$, $R_3$, and $R_4$ is not at the same time a straight or branched hydrocarbon chain having from 1 to 20 carbon atoms and which is saturated or contains from 1 to 3 double bonds; and when each of $R_2$ and $R_4$ represents the group

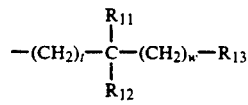

$R_{12}$ does not have the same meaning as $R_{13}$; and $R_{12}$ and $R_{13}$ are not a 9-fluorenyl substituent at the same time.

* * * * *

UNITED STATES PATENT AND TRADEMARK OFFICE
CERTIFICATE OF CORRECTION

Patent No: 5,153,226
Dated: October 6, 1992
Inventor(s): Chucholowski et al.

It is certified that error appears in the above-identified patent and that said Letters Patent is hereby corrected as shown below:

Column 46, line 30, structure should read:

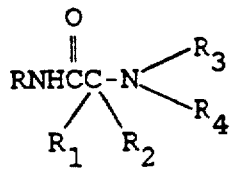

Column 46, line 39, insert the word "from" after "having".

Column 47, line 34, "t" should be "to".

Column 48, line 1, "from" should be "form".

Signed and Sealed this

Twelfth Day of October, 1993

BRUCE LEHMAN

Attest:

Attesting Officer

Commissioner of Patents and Trademarks